US010761053B2

United States Patent
Suri

(10) Patent No.: US 10,761,053 B2
(45) Date of Patent: Sep. 1, 2020

(54) NON-ENZYMATIC ELECTROCHEMICAL SENSOR FOR MEASURING ANALYTES

(71) Applicant: TERUMO KABUSHIKI KAISHA, Shibuya-ku, Tokyo (JP)

(72) Inventor: Jeff T. Suri, Fallbrook, CA (US)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 675 days.

(21) Appl. No.: 15/731,057

(22) PCT Filed: Apr. 23, 2015

(86) PCT No.: PCT/US2015/027250
§ 371 (c)(1),
(2) Date: Apr. 12, 2017

(87) PCT Pub. No.: WO2015/164578
PCT Pub. Date: Oct. 29, 2015

(65) Prior Publication Data
US 2017/0219521 A1  Aug. 3, 2017

Related U.S. Application Data

(60) Provisional application No. 61/983,188, filed on Apr. 23, 2014.

(51) Int. Cl.
*G01N 27/416* (2006.01)
*C07F 5/02* (2006.01)
(Continued)

(52) U.S. Cl.
CPC ......... *G01N 27/4168* (2013.01); *C07F 5/025* (2013.01); *G01N 27/4161* (2013.01);
(Continued)

(58) Field of Classification Search
CPC .......... G01N 27/4168; G01N 27/4161; G01N 27/3273; G01N 33/48707; G01N 33/66;
(Continued)

(56) References Cited

U.S. PATENT DOCUMENTS 7,799,912 B2 *  9/2010  Conoci ............... C07D 213/30
                                                    435/6.16
2005/0187097 A1 *  8/2005  Huang ............... G01N 27/3272
                                                    502/101
(Continued)

FOREIGN PATENT DOCUMENTS

JP    2004536279 A    12/2004
JP    2005516068 A     6/2005
(Continued)

OTHER PUBLICATIONS

Gamsey et al., The effect of boronic acid-positioning in an optical glucose-sensing ensemble, Tetrahedron, vol. 62, Issue 26, pp. 6321-6331 (2006) (Year: 2006).*

(Continued)

*Primary Examiner* — Maris R Kessel
*Assistant Examiner* — Vivian A Tran
(74) *Attorney, Agent, or Firm* — Kenja IP Law PC

(57) ABSTRACT

Embodiments described herein relate generally to compositions that include a synthetic redox-active receptor, and in particular to compositions that include a boronic acid based synthetic redox-active receptor which can electrochemically sense a target analyte in a sample solution. In some embodiments, a synthetic redox-active receptor can have a composition of formula I:

(Continued)

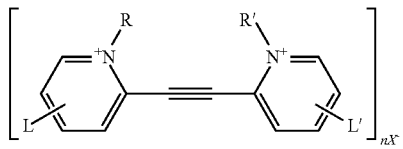

(I)

wherein the variables L, L', R, R', n and X⁻ are described herein.

10 Claims, 10 Drawing Sheets

(51) Int. Cl.
  *G01N 33/487* (2006.01)
  *G01N 33/66* (2006.01)
  *G01N 33/68* (2006.01)
  *G01N 33/94* (2006.01)
(52) U.S. Cl.
  CPC ....... *G01N 33/48707* (2013.01); *G01N 33/66* (2013.01); *G01N 33/6812* (2013.01); *G01N 33/9413* (2013.01)
(58) Field of Classification Search
  CPC ........... G01N 33/6812; G01N 33/9413; G01N 33/62–98; C07F 5/025
  See application file for complete search history.

(56) References Cited

U.S. PATENT DOCUMENTS

| | | | |
|---|---|---|---|
| 2006/0083688 A1* | 4/2006 | Singaram | B82Y 5/00 424/9.6 |
| 2011/0105866 A1 | 5/2011 | Markle et al. | |
| 2015/0366493 A1* | 12/2015 | Cremers | C12Q 1/005 600/345 |

FOREIGN PATENT DOCUMENTS

| | | |
|---|---|---|
| JP | 2011522266 A | 7/2011 |
| JP | 2013509944 A | 3/2013 |
| WO | 2008137604 A1 | 11/2008 |
| WO | 2010118711 A2 | 10/2010 |
| WO | 2011053247 A1 | 5/2011 |
| WO | 2015138690 A2 | 9/2015 |

OTHER PUBLICATIONS

Murakami et al., Electrochemical Saccharide Recognition by a Phenylboronic Acid-Terminated Redox Active Self-Assembled Monolayer on a Gold Electrode, Chemistry Letters, vol. 29, No. 8, pp. 940-941 (2000) (Year: 2000).*
Gamsey et al., Continuous Glucose Detection Using Boronic Acid-Substituted Viologens in Fluorescent Hydrogels: Linker Effects and Extension to Fiber Optics, Langmuir, vol. 22, pp. 9067-9074 (2006) (Year: 2006).*
Dec. 11, 2018, Notification of Reasons for Refusal issued by the Japan Patent Office in the corresponding Japanese Patent Application No. 2016-562818.
Sep. 17, 2019, Communication pursuant to Article 94(3) EPC issued by the European Patent Office in the corresponding European Patent Application No. 19154394.1.
Louis Adriaenssens et al., "Helquats: A Facile, Modular, Scalable Route to Novel Helical Dications", Chemistry A European Journal, 2009, pp. 1072-1076, vol. 15.
Nov. 20, 2017, The Extended European Search Report issued by the European Patent Office in the corresponding European Patent Application No. 15783437.5.
Oct. 25, 2016, International Preliminary Report on Patentability issued in the International Patent Application No. PCT/US2015/027250.
Oct. 28, 2015, International Search Report issued in the International Patent Application No. PCT/US2015/027250.
Xin Wu et al., "Selective sensing of saccharides using simple boronic acids and their aggregates", Chem Soc Rev, Oct. 21, 2013, pp. 8032-8048, vol. 42, RSC Publishing.
Nov. 26, 2019, Office Action issued by the Intellectual Property India in the corresponding Indian Patent Application No. 201617039117.
Dec. 27, 2017, Office Action issued by the China National Intellectual Property Administration in the corresponding Chinese Patent Application No. 201580020903.9.
Sep. 30, 2018, Office Action issued by the China National Intellectual Property Administration in the corresponding Chinese Patent Application No. 201580020903.9.
Mar. 17, 2020, Notification of Reasons for Refusal issued by the Japan Patent Office in the corresponding Japanese Patent Application No. 2019-073023.

* cited by examiner

NON-ENZYMATIC ELECTROCHEMICAL SENSOR FOR MEASURING ANALYTES

PRIORITY

The present application claims priority to U.S. Provisional Application 61/983,188, filed Apr. 23, 2014, the contents of which is hereby incorporated by reference in its entirety.

BACKGROUND

Embodiments described herein relate generally to compositions that include diquaternary ammonium salts, and in particular to compositions that include a boronic acid based synthetic redox-active receptor that can electrochemically sense a target analyte in a sample solution.

Electrochemical sensors are defined as sensors that employ an electronic parameter, for example, current, voltage, capacitance, impedance, or any other electronic parameter to measure the concentration of a target analyte, for example, a chemical, a biochemical, or a biological analyte. Among these electrochemical sensors, amperometric electrochemical sensors (i.e., current measuring sensors) are most common. Amperometric electrochemical sensors can include a working electrode, a reference electrode and optionally, a counter electrode, which can be electronically coupled via an electrical circuit, for example, a potentiostat. The working electrode is biased at a predetermined positive (i.e., oxidation) or a predetermined negative (i.e., reduction) voltage, capable of oxidizing or reducing the target analyte, respectively. The redox reaction produces a current that is measured and compared with calibration plots to determine the concentration of the target analyte.

Known amperometric electrochemical sensors are also used as biosensors for sensing non-electroactive target analytes, for example, a biomolecule such as glucose. Such known amperometric electrochemical sensors can include a biosensing molecule such as, for example, an enzyme or a synthetic biocatalyst immobilized on the surface of the working electrode. The biosensing molecule can catalytically decompose the non-electroactive biomolecule to yield an electroactive molecule and a by-product. For example, glucose oxidase decomposes glucose to yield gluconic acid, which is non-electroactive, and hydrogen peroxide which is electroactive. The electroactive hydrogen peroxide is oxidized or reduced on the surface of the working electrode to produce a current which is measured and is correlated to the concentration of the target analyte.

Electrochemical biosensors that include conventional biosensing molecules however, suffer from numerous drawbacks. The conventional biosensing molecules, for example, enzymes, can decompose or degrade over a period of time, or when exposed to non-physiological conditions leading to degradation of the sensitivity and resolution provided by the biosensor. Conventional enzymatic-based biosensors create by-products making them susceptible to biofouling, which can reduce the diffusion of the target analyte to the biosensing molecule and/or the working electrode and degrade the electrochemical signal. Furthermore, conventional biosensing molecules consume the target analyte during the redox reaction. This can make it difficult to sense very small concentrations of the target analyte and thereby negatively impact the limit of the detection of conventional biosensors.

Thus, it is an enduring goal of electrochemical sensing systems to develop new electrochemical sensors and biosensing molecules for in vitro and in vivo measurement that can provide a higher signal to noise ratio, longer life, and do not consume the target analyte.

SUMMARY

Embodiments described herein relate generally to compositions that include diquaternary ammonium salts, and in particular to compositions that include boronic acid-based synthetic redox-active receptors that can electrochemically sense a target analyte in a sample solution.

For instance, in one embodiment, the disclosure relates to a compound of Formula (1):

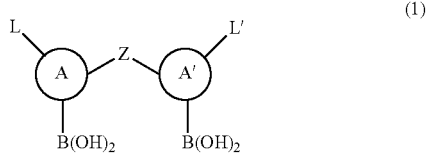

wherein:

A and A' are independently heteroaryl and comprise at least one nitrogen atom,

Z is a carbon linker consisting of $C_1$-$C_6$alkyl, $C_2$-$C_6$alkenyl, or $C_2$-$C_6$alkynyl groups L and L' are independently selected from the group consisting of —C(O)—, —C(O)—O, —(CH$_2$)$_m$—, —C(=CH$_2$)—, —C(O)—NH—, —NH—C(O)—, —O—, —S—, =CH— and —CH=, wherein m is an integer from 1 to 20.

In various embodiments, A and A' are selected from the group consisting of purinyl, indolyl, pyridinyl, bipyridyl, pyrimidinyl, azaindoylyl, pyrrolyl, pyrazinyl, pyridazinyl, isoindolyl, benzimidazolyl, imidazolyl and indazolyl.

In some embodiments, a composition can include a salt of any one of formulas I-VIII:

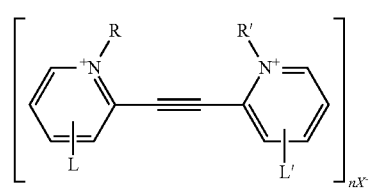

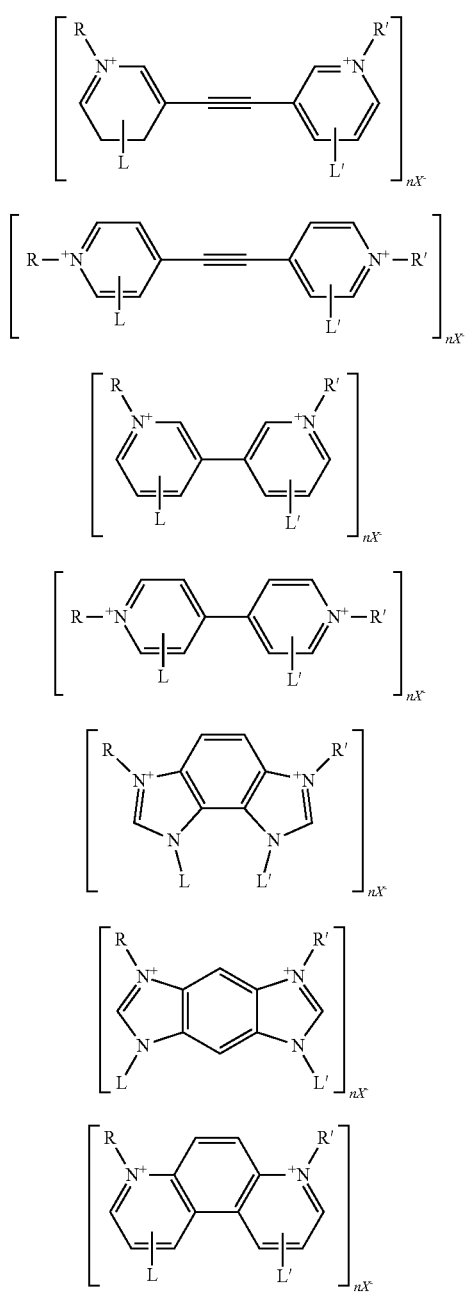

where:

X⁻ is an anion;

R and R' are independently —(CH$_2$)$_p$—R$^1$;

R$^1$ is C$_1$-C$_6$ alkyl-B(OR$^2$)(OR$^3$), aryl-B(OR$^2$)(OR$^3$), heteroaryl-B(OR$^2$)(OR$^3$), or heterocyclyl-B(OR$^2$)(OR$^3$);

R$^2$ and R$^3$ are independently H, C$_1$-C$_6$ alkyl or R$^2$ and R$^3$ can combine with the B atom to form a ring system;

L and L' are independently H, halogen, OH, CN, C$_1$-C$_6$ alkyl, C$_2$-C$_6$ alkenyl, C$_2$-C$_6$ alkynyl, aryl, heteroaryl, heterocyclyl, cycloalkyl, alkylthio, arylthio, alkoxy, aryloxy, —COOR$^4$, NH$_2$, —C(O)N(H)—(CH$_2$)$_p$—N(H)C(O)—R$^4$, —C(O)NH(R$^4$), or —N(H)C(O)R$^4$;

R$^4$ is independently at each occurrence H, C$_1$-C$_6$ alkyl, C$_2$-C$_6$ alkenyl, C$_2$-C$_6$ alkynyl, aryl, heteroaryl, heterocyclyl, or cycloalkyl;

n is 2, 3, 4, 5, or 6; and p is independently 0, 1, 2, 3, 4, 5, or 6.

DETAILED DESCRIPTIONS

Figure 1:
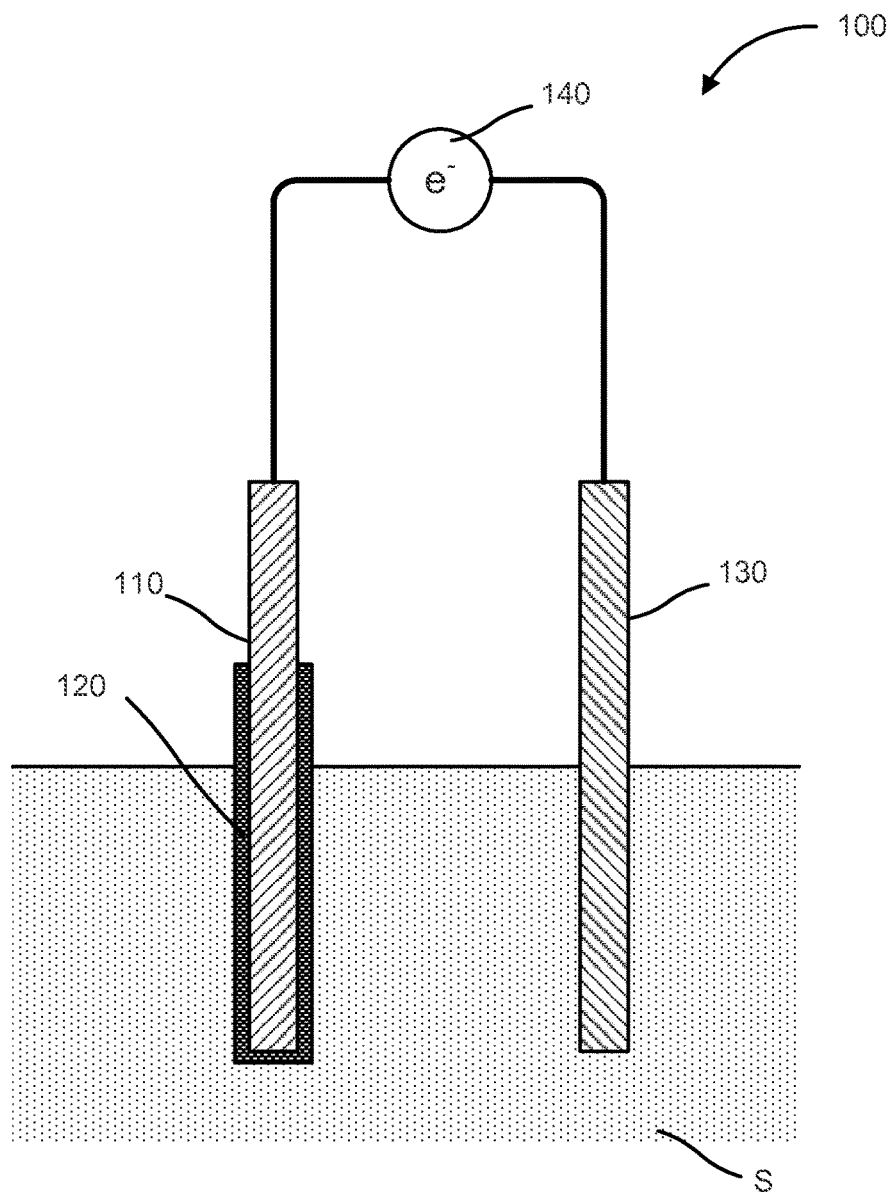
FIG. 1 is a schematic illustration of an electrochemical sensing system, according to an embodiment.

Embodiments described herein relate generally to compositions that include a diquaternary ammonium salt, and in particular to compositions that include a boronic acid based synthetic redox-active receptor that can electrochemically sense a target analyte in a sample solution. Conventional amperometric electrochemical sensors are configured to sense a non-electroactive target analyte, for example, a biomolecule such as glucose. Such electrochemical sensors can include one or more biosensing molecules such as, for example, an enzyme or a synthetic biocatalyst immobilized on the surface of the working electrode. The biosensing molecules can catalytically decompose the non-electroactive biomolecule to yield an electroactive molecule. The electroactive molecule can undergo an electrochemical redox reaction on a working electrode biased at an appropriate biasing voltage, and produce a measurable redox current corresponding to the concentration of the target analyte. Conventional biosensing molecules however, suffer from numerous drawbacks. For example, conventional biosensing molecules can decompose or degrade over a period of time, are susceptible to biofouling, create by-products, and consume the target analyte during redox reaction. These drawbacks can negatively impact the sensitivity, selectivity, limit of detection, and/or shelf life of the conventional electrochemical sensors.

Embodiments of the compositions described herein provide several advantages over conventional biosensing molecules such as, for example: (1) reversible binding with the target analyte such that the target analyte is not consumed; (2) maintaining its activity in non-physiological environments, thereby providing longer shelf life; and (3) interaction with the target analyte such that no by-products are produced thereby limiting fouling of the working electrode on which the synthetic redox-active receptor is disposed. Embodiments of the compositions described herein can be used in an electrochemical sensing system that includes a rhodium working electrode. Examples of such electrochemical sensing systems are described in U.S. Provisional Patent Application No. 61/951,665, entitled "Electrochemical Sensing System," filed Mar. 12, 2014, the entire contents of which are incorporated herein by reference in its entirety. Embodiments of the synthetic redox-active receptor described herein can also be included in wearable devices that can be disposed on a user, for example, to enable real time measurement of a target analyte. Examples of such electrochemical sensing systems are described in U.S. Provisional Patent Application No. 61/951,667, entitled "Wearable Electrochemical Sensor and Methods," filed Mar. 12, 2014, the entire contents of which are incorporated herein by reference in their entirety.

In some embodiments, a composition can include a salt of any one of formulas I-VIII:

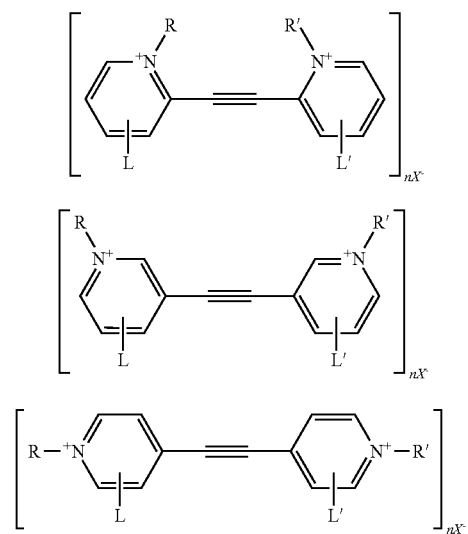

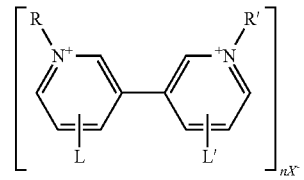

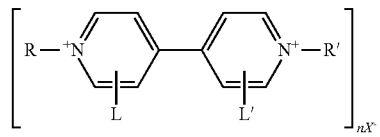

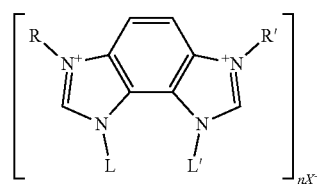

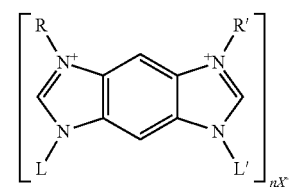

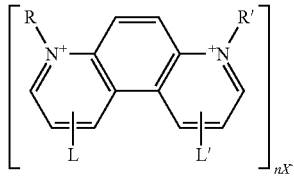

where:

$X^-$ is an anion;

R and R' are independently $-(CH_2)_p-R^1$;

$R^1$ is $C_1$-$C_6$ alkyl-$B(OR^2)(OR^3)$, aryl-$B(OR^2)(OR^3)$, heteroaryl-$B(OR^2)(OR^3)$, or heterocyclyl-$B(OR^2)(OR^3)$;

$R^2$ and $R^3$ are independently H, $C_1$-$C_6$ alkyl or $R^2$ and $R^3$ can combine with the B atom to form a ring system;

L and L' are independently H, halogen, OH, CN, $C_1$-$C_6$ alkyl, $C_2$-$C_6$ alkenyl, $C_2$-$C_6$ alkynyl, aryl, heteroaryl, heterocyclyl, cycloalkyl, alkylthio, arylthio, alkoxy, aryloxy, $-COOR^4$, $NH_2$, $-C(O)N(H)-(CH_2)_p-N(H)C(O)-R^4$, $-C(O)NH(R^4)$, or $-N(H)C(O)R^4$;

$R^4$ is independently at each occurrence H, $C_1$-$C_6$ alkyl, $C_2$-$C_6$ alkenyl, $C_2$-$C_6$ alkynyl, aryl, heteroaryl, heterocyclyl, or cycloalkyl;

n is 2, 3, 4, 5, or 6; and p is independently 0, 1, 2, 3, 4, 5, or 6.

In some embodiments, a process for preparing a salt of formula I: includes providing a precursor having the formula:

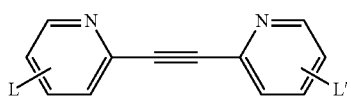

and contacting the precursor with an electrophile X—(CH$_2$)$_p$—R$^1$ under conditions effective to form the salt of formula I.

In some embodiments, an electrochemical sensing system can include a working electrode. A composition is disposed on the working electrode which is formulated to reversibly associate with a target analyte such that the target analyte does not decompose. The composition can have a first redox potential in the absence of a target analyte and a second redox potential different than the first redox potential in the presence of the target analyte. The electrochemical sensing system can also include a reference electrode and an electrical circuit electronically coupled to the working electrode and the reference electrode. The electrical circuit can be operable to (a) bias the working electrode in the range of about −0.7 volts to about +0.4 volts and (b) measure a current corresponding to the concentration of the target analyte.

In some embodiments, the biasing voltage is about −0.7 volts. In some embodiments, the biasing voltage is about −0.6 volts. In some embodiments, the biasing voltage is about −0.5 volts. In some embodiments, the biasing voltage is about −0.4 volts. In some embodiments, the biasing voltage is about −0.35 volts. In some embodiments, the biasing voltage is about −0.3 volts. In some embodiments, the biasing voltage is about 0 volts. In some embodiments, the biasing voltage is less than about 0.4 volts.

In one or more embodiments, the electrochemical sensing system can comprise a polymer. In one or more embodiments, the electrochemical sensing system can comprise a redox-active molecule. In one or more embodiments, the redox-active molecule can be a boronic acid. In one or more embodiments, the redox-active molecule can be a quaternary ammonium salt. In one or more embodiments, the analyte concentration is determined via amperometric measurement. In one or more embodiments, the analyte concentration is determined via pulsed amperometric measurement. In one or more embodiments, the analyte concentration is determined via differential pulse measurement. In one or more embodiments, the analyte concentration is determined via potentiometry. In one or more embodiments, at least a portion of the working electrodes comprises at least one of rhodium, gold, platinum, or palladium.

As used herein, the term "about" and "approximately" generally mean plus or minus 10% of the value stated, e.g., about 250 μm would include 225 μm to 275 μm, about 1,000 μm would include 900 μm to 1,100 μm.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$alkyl, —C$_1$-C$_6$alkyl, —OC$_2$-C$_6$alkenyl, —OC$_2$-C$_6$alkynyl, —C$_2$-C$_6$alkenyl, —C$_2$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, —NH$_2$, —NH(C$_1$-C$_6$alkyl), —N(C$_1$-C$_6$alkyl)$_2$, —S(O)$_2$—C$_1$-C$_6$alkyl, —S(O)NHC$_1$-C$_6$alkyl, and —S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

The term "heteroaryl" means a monovalent monocyclic or bicyclic aromatic radical of 5 to 12 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom(s) is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two or more fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

"Alkyl" refers to a straight or branched chain saturated hydrocarbon. C$_1$-C$_6$alkyl groups contain 1 to 6 carbon atoms. Examples of a C$_1$-C$_6$alkyl group include, but are not limited to, methyl, ethyl, propyl, butyl, pentyl, isopropyl, isobutyl, sec-butyl and tert-butyl, isopentyl and neopentyl.

"Alkylenyl" as herein defined refers to groups of general formula —(CH$_2$)n- where n is an integer from 1 to 6. Suitable examples of alkylenyl groups include methylenyl, ethylenyl, and propylenyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A C$_2$-C$_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

As used herein, the term "target analyte" refers to a chemical or a biochemical that can be sensed by embodiments of the electrochemical sensing system described herein.

As used herein, the term "electroactive" means a chemical or a biochemical that can be electrochemically oxidized or reduced at an electrode biased at an appropriate biasing voltage.

As used herein, the term "interferents" refers to chemicals or biochemicals (except a target analyte) that are electroactive and can undergo a redox reaction at a working electrode included in any embodiments of the electrochemical sensing system described herein, and that contributes to noise.

In some embodiments, a synthetic redox-active receptor can include a salt of any one of formulas I-VIII:

I

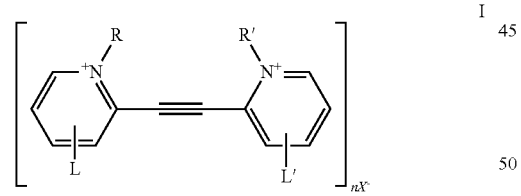

II

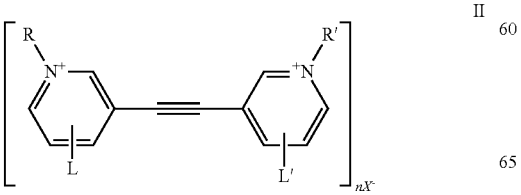

III

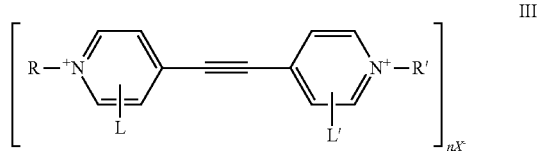

IV

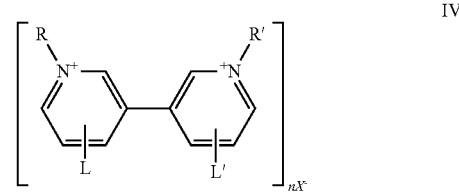

V

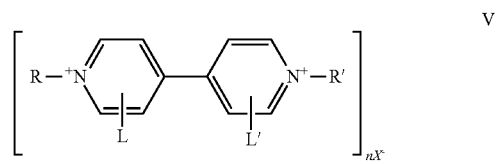

VI

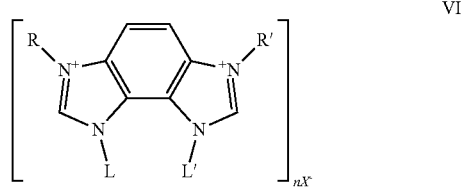

VII

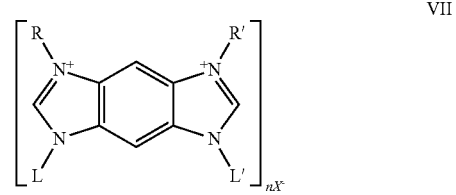

VIII

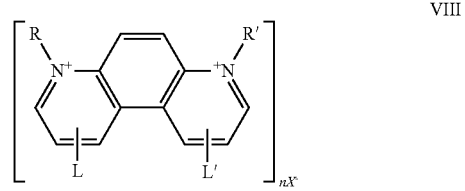

where $X^-$ is an anion, for example, an anion selected form the group including $Br^-$, $Cl^-$, $I^-$, $F^-$, $PF_6^-$, sulfonate, mesylate, or triflate.

R and R' are independently —$(CH_2)_p$—$R^1$; $R^1$ is $C_1$-$C_6$ alkyl-B(OR$^2$)(OR$^3$), $C_2$-$C_6$ alkenyl-B(OR$^2$)(OR$^3$), $C_2$-$C_6$ alkynyl-B(OR$^2$)(OR$^3$), cycloalkyl-B(OR$^2$)(OR$^3$), heterocyclyl-B(OR$^2$)(OR$^3$), aryl-B(OR$^2$)(OR$^3$), or heteroaryl-B(OR$^2$)(OR$^3$).

R$^2$ and R$^3$ are independently H, C$_1$-C$_6$ alkyl or R$^2$ and R$^3$ can combine with the B atom to form a ring system. In some embodiments, R and R' can be receptors that can associate with a target analyte such as, for example, glucose, glutamate, lactic acid, dopamine, diols, alpha hydroxy acids or any other target analyte capable of interacting, coordinating, binding, or otherwise associating with R and R'. In such embodiments, the salts of any one of formula I—VIII can be used for sensing a target analyte. For example, the salts of any one of formulas I—VIII can be included in an electrochemical sensor for amperometrically sensing a target analyte (e.g., glucose).

L and L' are independently H, halogen, OH, CN, C$_1$-C$_6$ alkyl, C$_2$-C$_6$ alkenyl, C$_2$-C$_6$ alkynyl, aryl, heteroaryl, heterocyclyl, cycloalkyl, —COOH, NH$_2$, —C(O)N(H)—(CH$_2$)$_o$-N(H)C(O)—R$^4$, —C(O)NH(R$^4$), or —N(H)C(O)R$^4$. R$^4$ is independently at each occurrence H, C$_1$-C$_6$ alkyl, C$_2$-C$_6$ alkenyl, C$_2$-C$_6$ alkynyl, aryl, heteroaryl, heterocyclyl, or cycloalkyl. In some embodiments, L and L' can be linkers for immobilizing the salts of any one of formulas I-VIII, for example, immobilization within a polymer matrix or on a solid surface (e.g., a surface of a metallic electrode such as, for example, a gold, platinum, silver, rhodium, palladium, nickel, chromium, copper, or any other metallic electrode). In such embodiments, the L and L' linkers can, for example, enable the formation of a self-assembled monolayer of the salts of formulas I-VIII on a surface, for example, the surface of a working electrode included in an electrochemical sensing system.

Furthermore, n is 2, 3, 4, 5, or 6, and p is independently 0, 1, 2, 3, 4, 5, or 6.

In some embodiments, p can be equal to 1. In some embodiments, R$^1$ can be an aryl such as, for example, aryl-B(OR$^2$)(OR$^3$).

In some embodiments, the composition can be a bipyridinium alkyne boronic acid having the structure P-1:

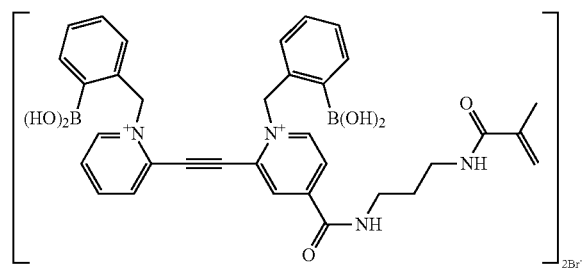

(P-1)

In some embodiments, the synthetic redox-active receptor can be a boronic acid functionalized bipyridinium having the structure P-2:

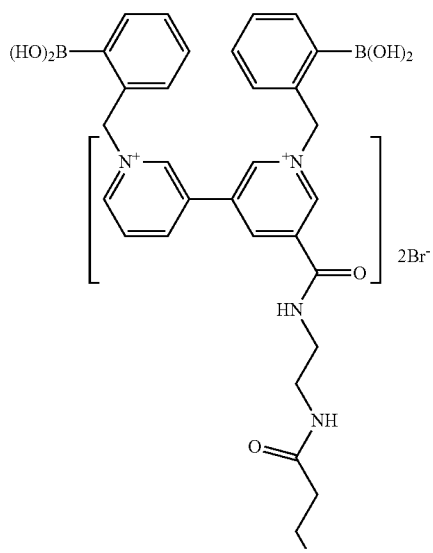

(P-2)

In some embodiments, the salt of any one of formulas I-VIII can be formulated such that R$^1$ is ortho-, meta-, or para-substituted phenylboronic acid, nitrophenylboronic acid, fluorophenyl boronic acid, chlorophenyl boronic acid, methoxyphenylboronic acid, aminophenylboronic acid, carboxyphenylboronic acid, hydroxyphenylboronic acid, methylphenylboronic acid, dimethylphenylboronic acid, bromophenylboronic acid, or vinylboronic acid.

In some embodiments, the composition can comprise a compound of the formula Va:

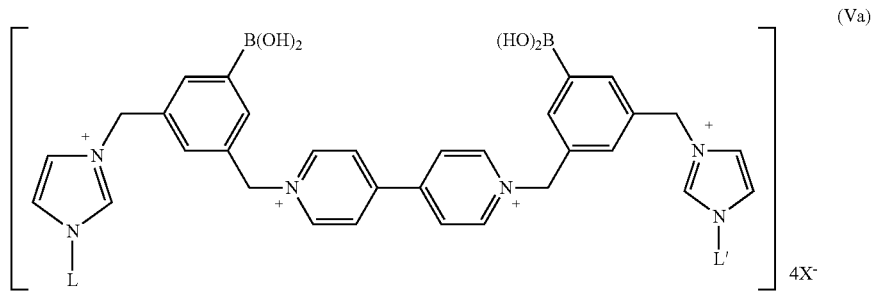

wherein L is as defined above.

In some embodiments, the salt of any one formulas I—VIII can be formulated such that, for example, L' is —C(O)N(H)—(CH$_2$)$_o$—N(H)C(O)—R$^4$. In some embodiments, the salts of any one of formulas I—VIII can be formulated such that, for example, L' is —C(O)N(H)—(CH$_2$)$_3$—N(H)C(O)—R$^4$ and R$^4$ is 2-propenyl.

The salt of formula I can be prepared using any suitable process. In some embodiments, a process for preparing the salt of formula I can include providing a precursor having the formula:

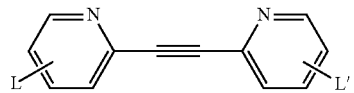

and contacting the precursor with a Lewis Acid X—(CH$_2$)$_p$—R$^1$ under condition effective to form the salt of formula I.

For example, in some embodiments, the salt of formula I can be a bipyridinium alkyne boronic acid and a process for preparing the bipyridinium alkyne boronic acid can include Scheme 1, below:

Scheme 1

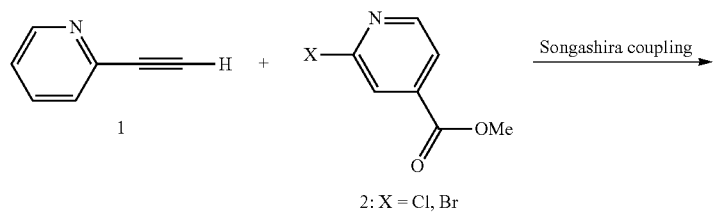

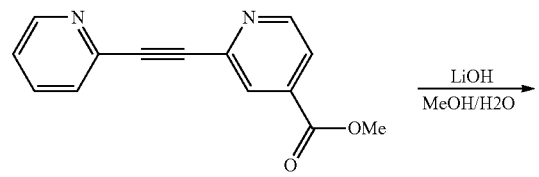

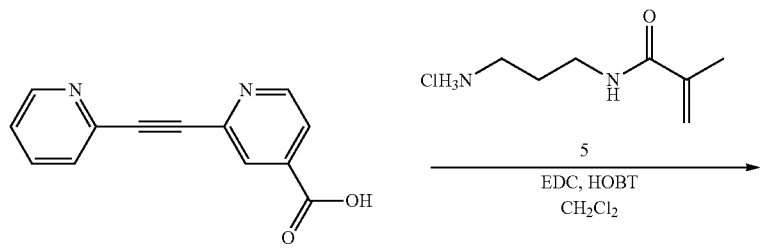

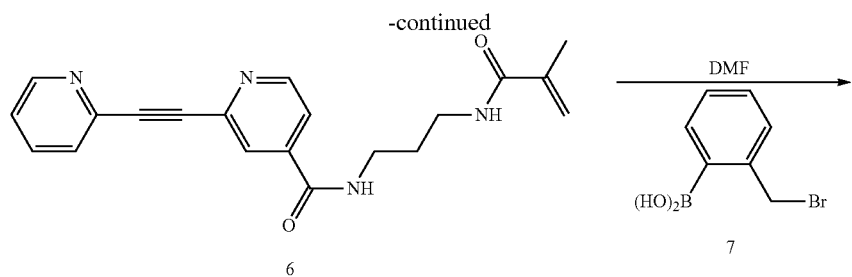

8: bipyridinium alkyne boronic acid

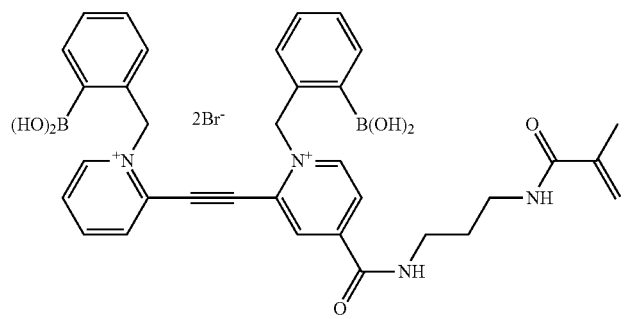

The salts of formula II-VIII can be prepared using any suitable process. In some embodiments, a process for preparing the salt of any one of formulas II-VIII can include providing a suitable precursor and contacting the precursor with an electrophile X—(CH$_2$)$_p$—R$^1$ under conditions effective to form the salt of formulas II-VIII.

In some embodiments, the salt of formula VII can be a benzo-bis(imidazolium) boronic acid and a process for preparing the benzo-bis(imidazolium) boronic acid can include the Schemes 2 and 3, below:

Scheme 2

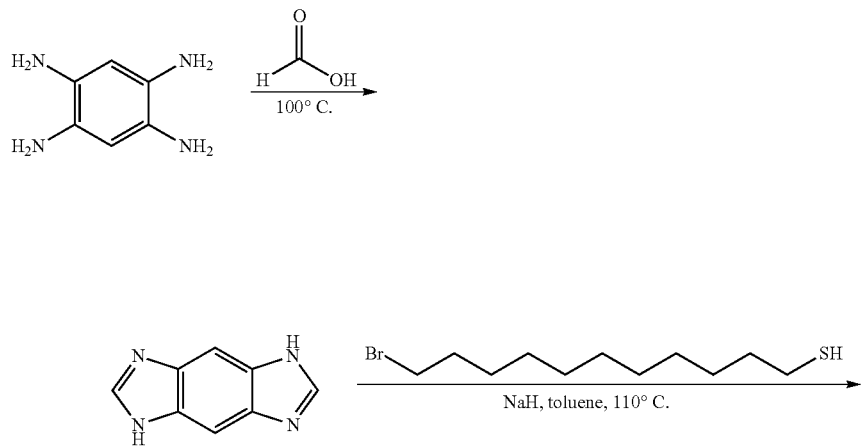

17 18
-continued
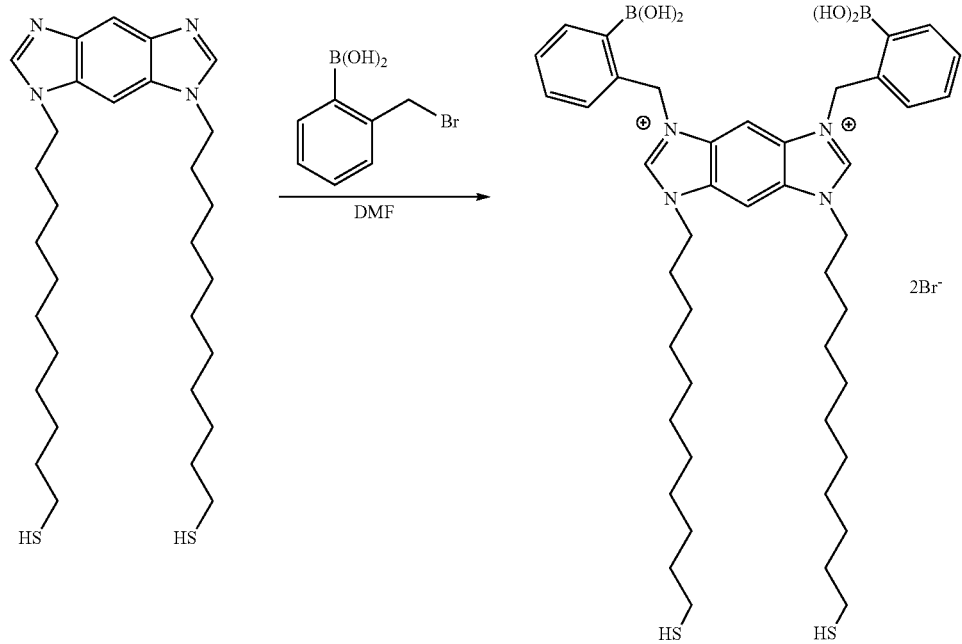
Scheme 3
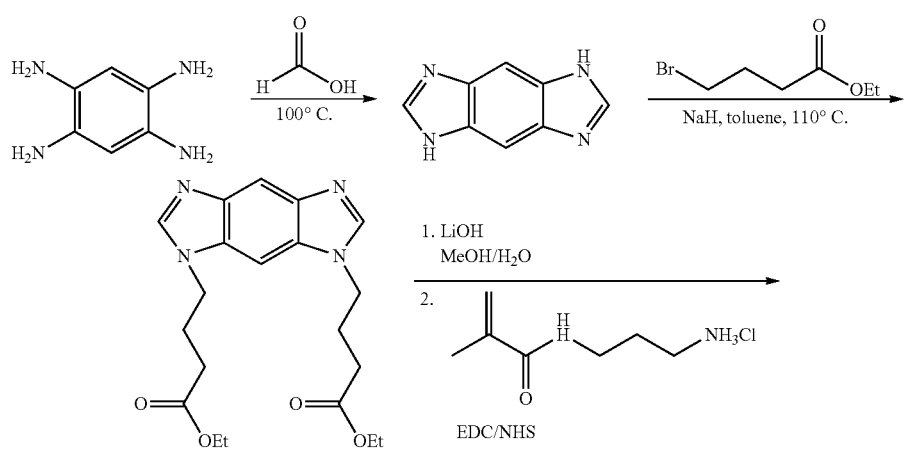
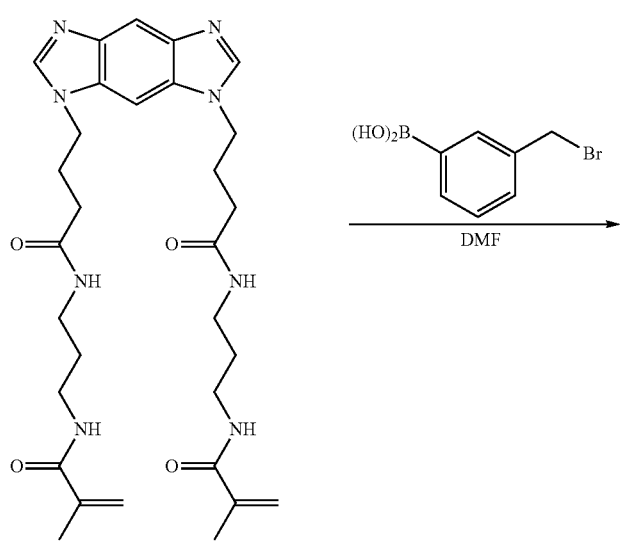

-continued

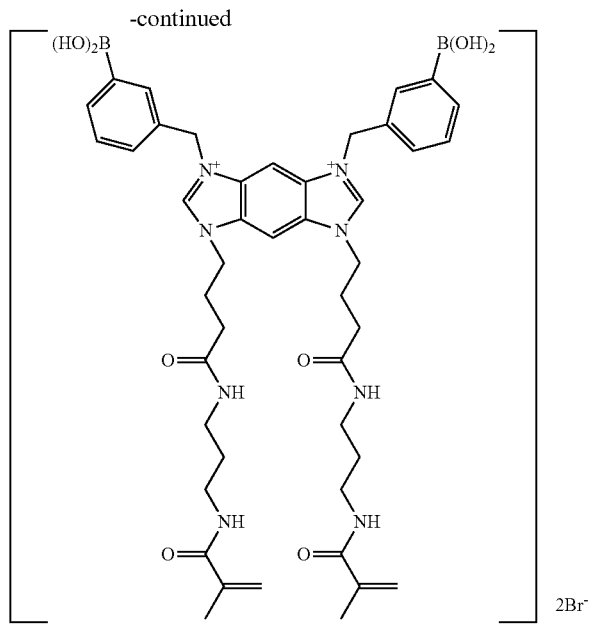

In some embodiments, the any one of the salts of formula I-VIII, for example, a bipyridinium alkyne boronic acid can be redox active. For example, the salts of formulas I-VIII can be capable of accepting an electron, for example, an electron donated by an electrode biased at an appropriate biasing voltage. The redox capability of the salts of formulas I-VIII can change on interacting, coordinating, binding, or otherwise associating with a target analyte, for example, glucose, glutamate, lactic acid, dopamine or a diol. This property of the salts of formulas I-VIII can be used for sensing a target analyte in an electrochemical sensing system, as described herein.

FIG. 1 shows a schematic illustration of an electrochemical sensing system 100, according to an embodiment. The electrochemical system 100 includes a working electrode 110, a reference electrode 130 and an electrical circuit 140. A composition 120 is disposed on the working electrode 110. The electrochemical sensing system 100 can be configured to interact with a non-electroactive target analyte included in a sample S and measure a redox current corresponding to a concentration of the target analyte.

The working electrode 110 can include any suitable electrode capable of communicating electrons to or accepting electrons from the composition 120. In some embodiments, at least a portion of the working electrode 110 can be formed from rhodium, platinum, palladium, gold, silver, nickel, chromium, copper iridium, ruthenium carbon, graphite, carbon nanotubes, graphene, any other suitable conductive material or combination thereof. In some embodiments, the working electrode 110 can be formed from an oxide of rhodium, for example $RhO_2$, $Rh(OH)_3$ or $Rh_2O_3$. In some embodiments, a blend of rhodium and another metal, for example, ruthenium, platinum, palladium, gold, nickel, any other suitable metal or alloy, can be used to form the working electrode 110.

The working electrode 110 can have any suitable shape or size. For example, in some embodiments, the working electrode 110 can be a rod having a circular, oval, or polygonal cross-section. In such embodiments, the working electrode 110 can be a solid cylindrical electrode or a hollow cylindrical electrode (e.g., a cylindrical electrode that defines a lumen). In some embodiments, the working electrode 110 can be a needle type electrode which can, for example, be configured to be inserted into an animal or human body for measuring the concentration of the target analyte. In some embodiments, the working electrode 110 can be a flat electrode, for example, a flat plate, a disc, a solid state microfabricated electrode (e.g., of the type used in MEMS devices), or a screen printed electrode. In some embodiments, at least a portion of the working electrode 110 can be insulated with an insulating material, for example, rubber, TEFLON®, plastic, parylene, silicon dioxide, silicon nitride, any other suitable insulation material or combination thereof. The insulation material can, for example, be used to define an active area of the working electrode 110.

In some embodiments, the working electrode 110 can be subjected to a surface modification process to modify a surface area of the working electrode 110, for example, to provide a larger surface area for the electron transfer between the working electrode and the composition 120. Such surface modification processes can include, for example, etching (e.g., etching in an acidic or basic solution), voltage cycling (e.g., cyclic voltammetry), electrodeposition of colloidal metallic particles, and any other suitable surface modification process or combination thereof. In some embodiments, the working electrode 110 can be oxidized to yield a metal oxide (e.g., rhodium dioxide) layer on the substrate. For example, the working electrode 110 can be immersed in an acidic bath, exposed to an oxygen plasma, any other suitable process or combination thereof can be used to form a metal oxide on the surface of the working electrode 110.

In some embodiments, a selectivity layer (not shown) can be disposed on the working electrode 110, for example, disposed between the surface of the working electrode and the composition 120. The selectivity layer can be configured to prevent electroactive interferents from coming in contact with the working electrode 110 and undergoing a redox reaction. For example, in some embodiments, the selectivity layer can be configured to repel oppositely charged ionic interferents. For example, a NAFION® selectivity layer can be disposed between an outer surface of the working electrode 110 and the composition 120. The NAFION® is inherently negatively charged and repels negatively charged interferents such as, for example, ascorbic acid, from coming in contact with and undergoing a redox reaction at the working electrode 110. In some embodiments, the selectivity layer can be a size exclusion layer, for example, a cellulose acetate layer. Such a selectivity layer can be porous and define a pore size such that larger interferents such as, for example, ascorbic acid cannot pass through the pores and are prevented from coming in contact with and undergoing a redox reaction at the working electrode 110.

The composition 120 is disposed on the working electrode 110 and formulated to reversibly associate with the target analyte (e.g., glucose, glutamate, an alphahydroxy acid such as, for example, lactic acid, and a diol such as, for example dopamine etc.) such that the target analyte does not decompose. The composition 120 can be a synthetic redox-active receptor that is formulated to be movable between a reduced state and an oxidized state.

For example, the composition 120 can have a first redox potential in the absence of the target analyte and a second redox potential different from the first redox potential in the presence of the target analyte. In this manner, the composition 120 can be used to electrochemically sense a target analyte, as described herein in further detail.

In some embodiments, the composition 120 can include a salt having any one of formulas I-VIII, as described herein.

In some embodiments, the composition 120 can be bipyridinium alkyne boronic acid, having a structure P-1:

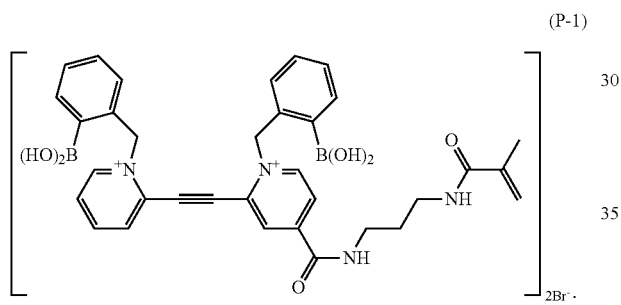

(P-1)

In some embodiments, the composition 120 can be a boronic acid bipyridinium having the general structure P-2:

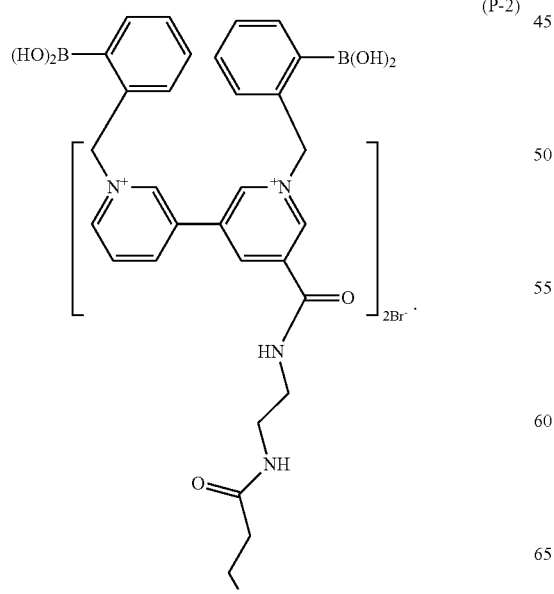

(P-2)

In some embodiments, the composition 120 can have a structure P-3:

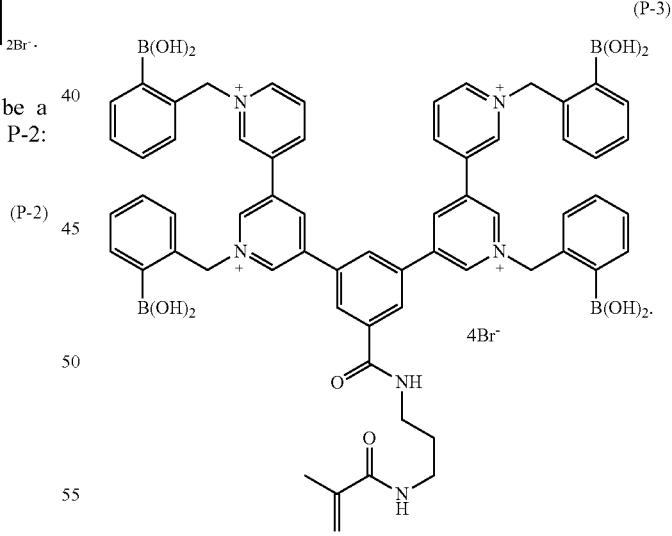

(P-3)

In some embodiments, the composition 120 can have a structure P-4:

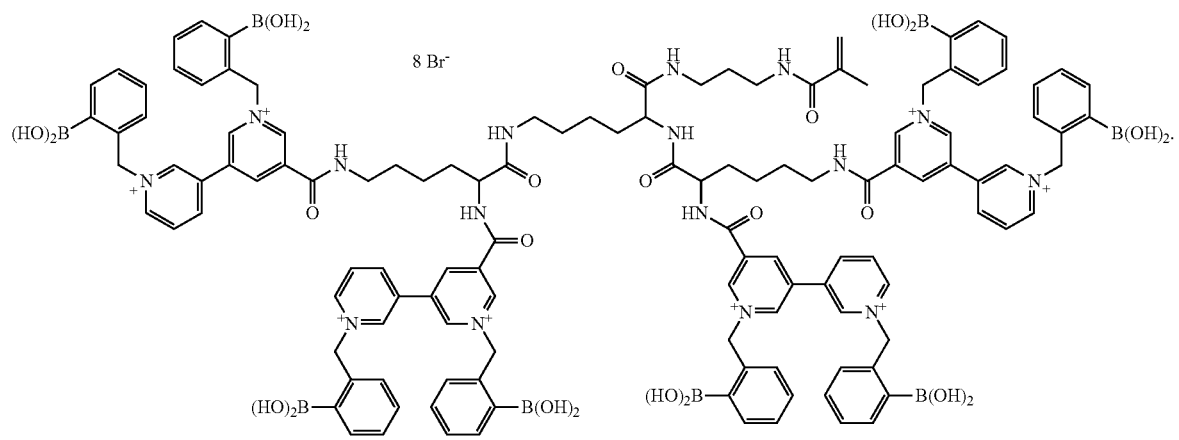
In some embodiments, the composition can have a structure P-5:
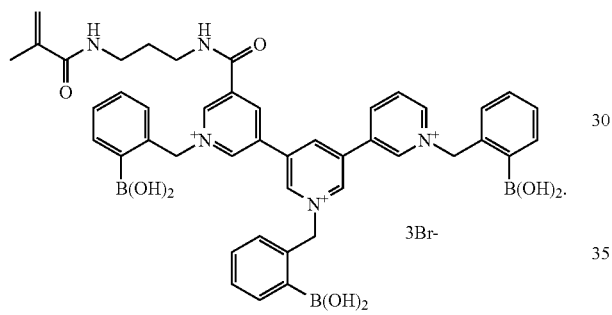
In some embodiments, the composition 120 can have a structure P-6:
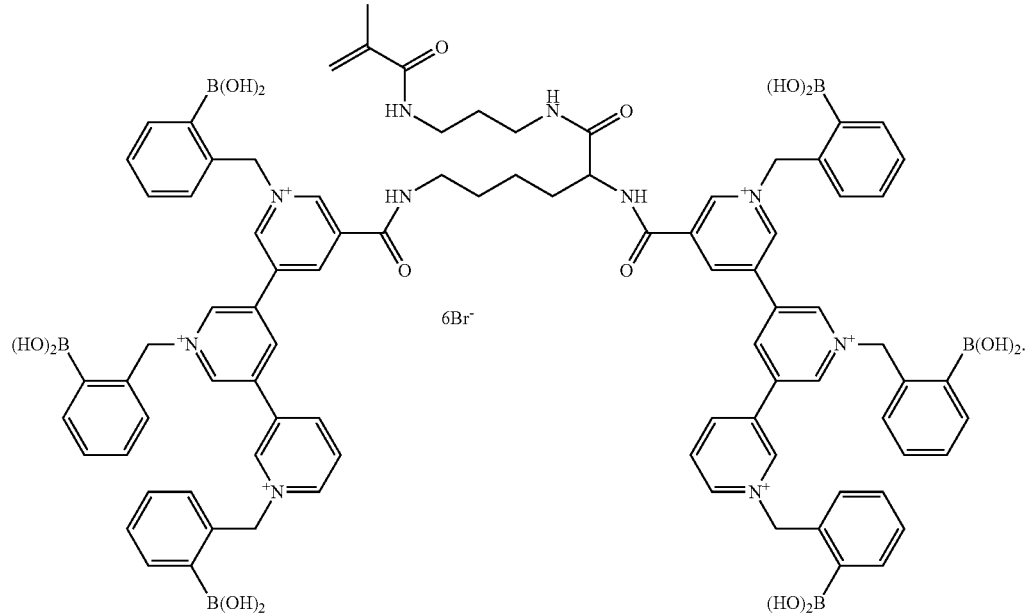

In some embodiments, the composition 120 can have a structure P-7:
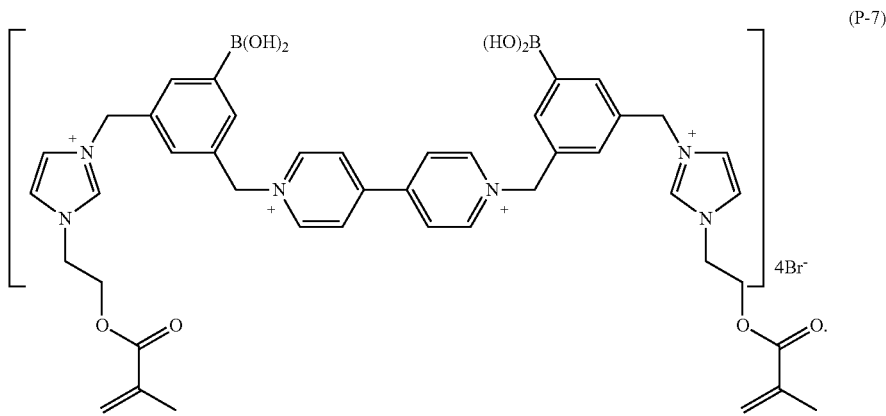
In some embodiments, the composition 120 can have a structure P-8:
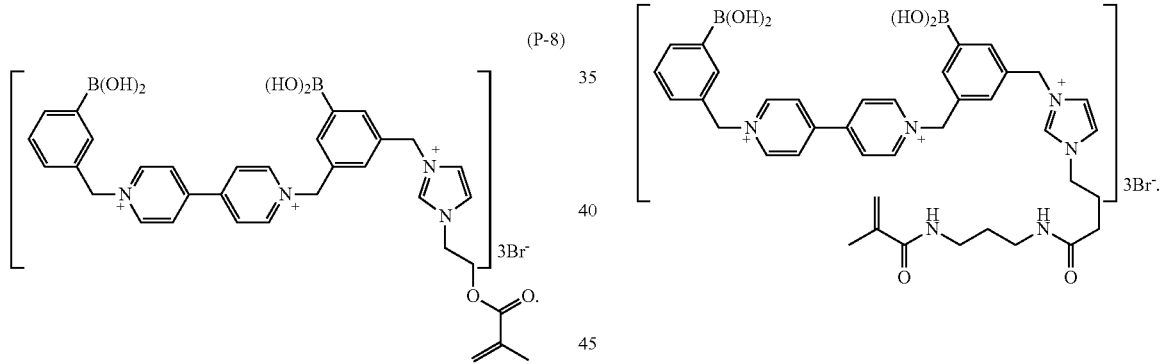
In some embodiments, the composition 120 can have a structure P-9:
In some embodiments, the composition 120 can have a structure P-10:
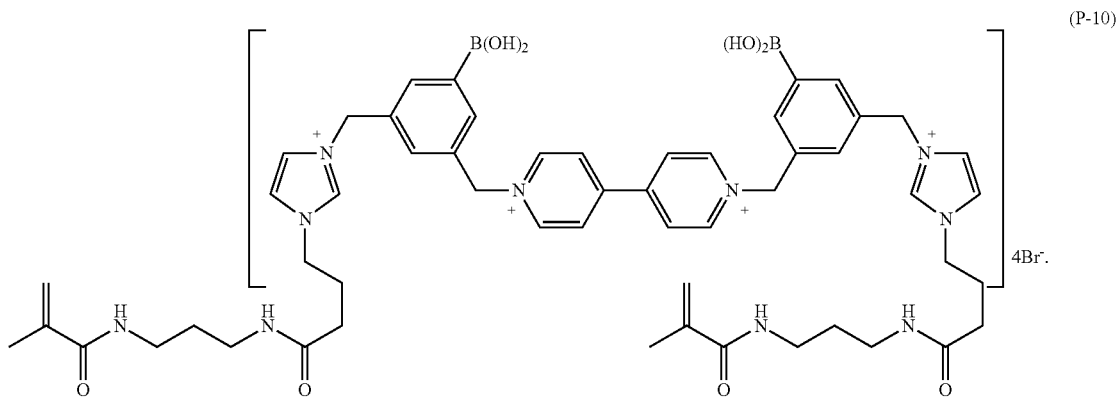

In some embodiments, the composition 120 can have a structure P-11:
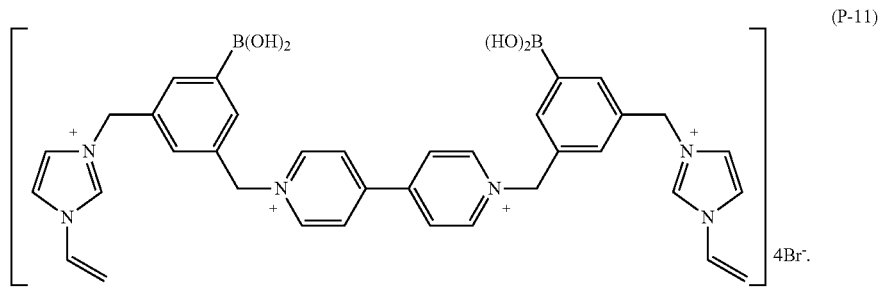
(P-11)
In some embodiments, the composition 120 can have a structure P-12:
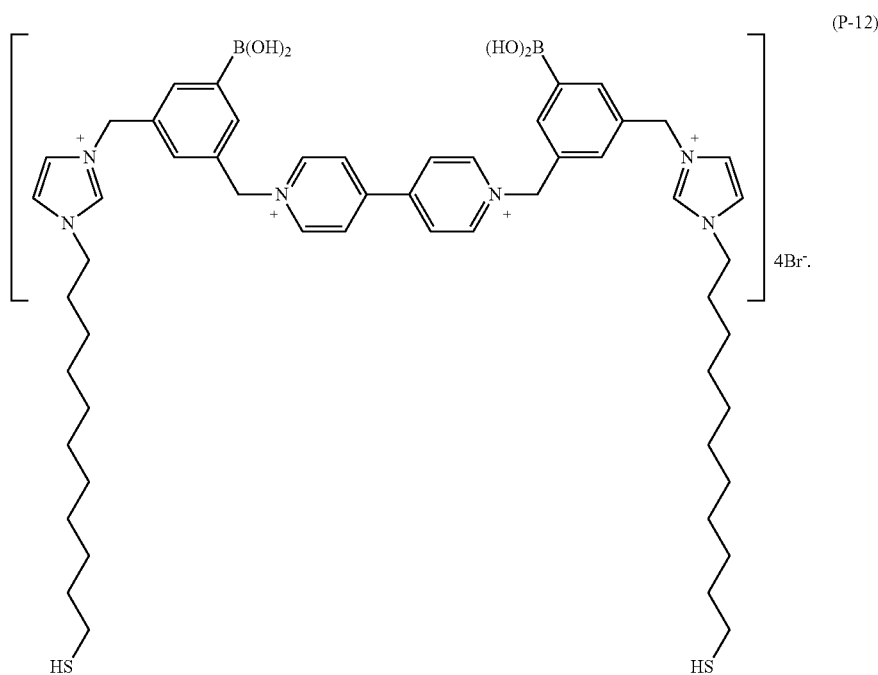
(P-12)
In some embodiments, the composition 120 can have a structure P-13:

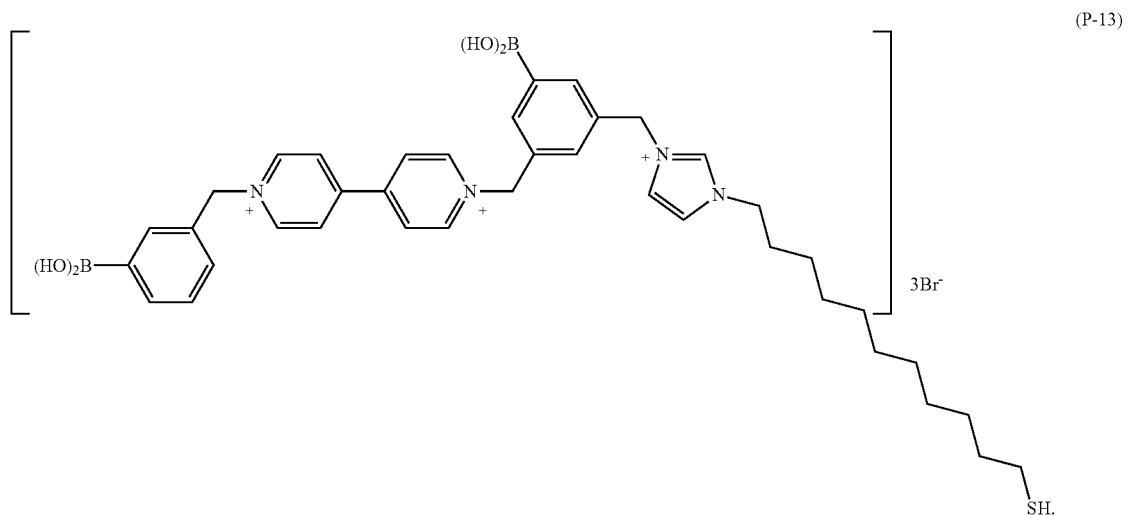
In some embodiments, the composition 120 can have a structure P-14:
In some embodiments, the composition 120 can have a structure P-15:
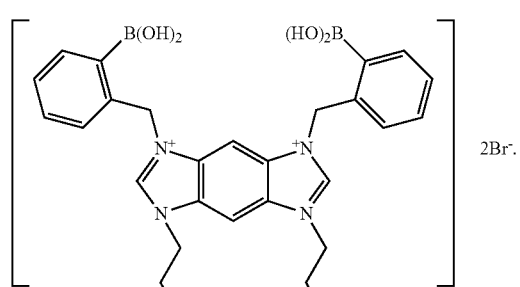
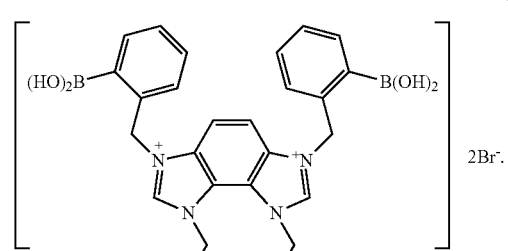

In some embodiments, the composition 120 can have a structure P-16:

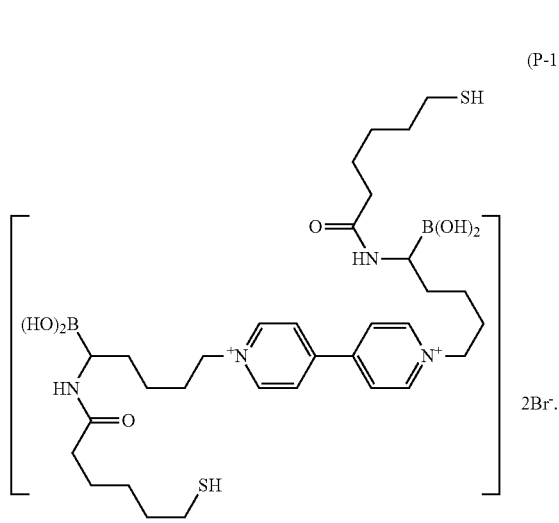

(P-16)

In some embodiments, the composition 120 can have a structure P-17:

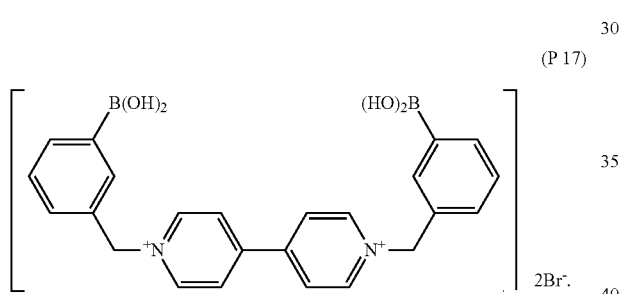

(P 17)

In some embodiments, the composition 120 can have a structure P-18:

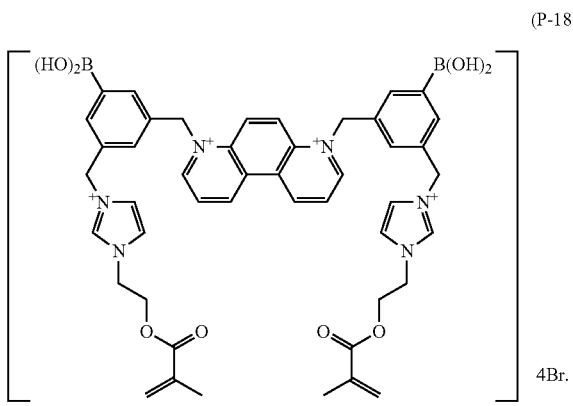

(P-18)

In some embodiments, the composition 120 has the structure P-19:

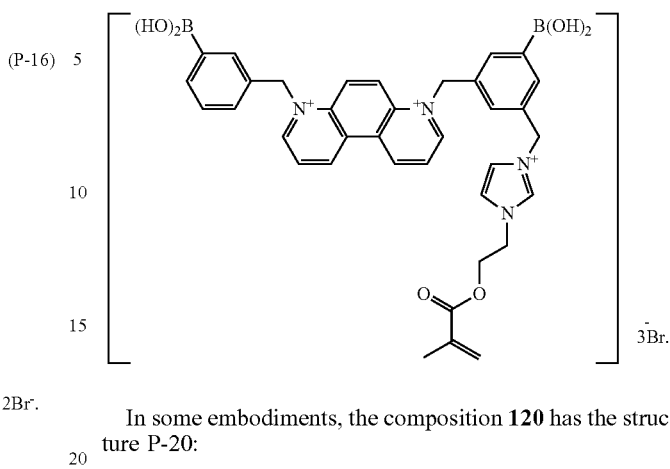

(P-19)

In some embodiments, the composition 120 has the structure P-20:

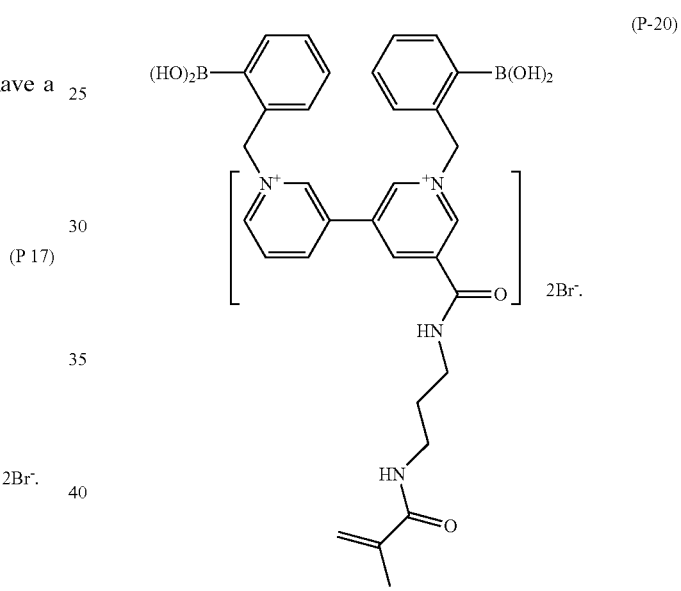

(P-20)

In some embodiments, the present disclosure provides the compound:

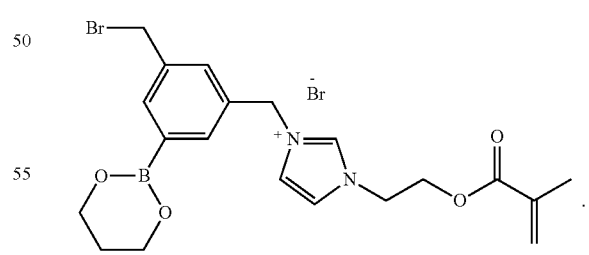

The composition 120 can be disposed on the working electrode 110 using any suitable means such that the composition 120 is fixedly disposed on the surface of the working electrode 110. In some embodiments, the composition 120 can be physically adsorbed on the surface. In some embodiments, the composition 120 can be covalently coupled to the surface of the working electrode 110, for example, using thiol chemistry. For example, the linkers L and L' in the salts of formulas I—VIII can be capable of forming covalent bonds with functional thiol alkanes (e.g., monodentate or multidentate thiols). In some embodiments, the composition 120 can be suspended in a porous membrane, for example, a polyurethane membrane, a silicone membrane, a silicone-polyurethane membrane, a glutaraldehyde membrane, a sol-gel membrane, a NAFION® membrane, a hydrogel membrane, any other suitable membrane or combination thereof. In some embodiments, the composition 120 can be coupled to a functional polymer layer or a cast film disposed on the working electrode 110, for example, using epoxide formation, 1-ethyl-3-(3-dimethylaminopropyl)carbodiimide (EDC) coupling, or click chemistry. In some embodiments, the composition 120 can be coupled to a prepolymer and cast as a film, for example, to form a redox-active polyurethane or silicone.

In some embodiments, the composition 120 can be suspended in a solution capable of forming a hydrogel or a sol-gel on the surface of the working electrode 110. For example, the hydrogel or sol-gel can be formulated to be photopolymerized (e.g., include an ultra-violet light polymerization initiator such as, for example, IRGACURE® 2959), polymerized using thermal initiation (e.g., include a low temperature initiator such as, for example, WAKO® VA-044, or redox polymerized (e.g., include a redox initiator such as, for example, persulfate-TEMED). The hydrogel or the sol-gel can be polymerized on the surface of the working electrode 110 such that the composition 120 is physically trapped and/or covalently bound within the hydrogel or sol-gel layer and is thereby, fixedly disposed on the surface of the working electrode 110.

In some embodiments, the composition 120 can be disposed on the working electrode 110 via an electroactive polymer. For example, the composition 120 can be formulated to be electropolymerized (e.g., include a radical initiator such as, for example, potassium persulfate), at a set bias voltage using the appropriate monomer (e.g., pyrole, thiophene, aniline, acetylene, or any other polymerizable monomer).

In some embodiments, the composition 120 can be disposed on the working electrode 110 using electrostatic interactions. For example, the composition 120 can be formulated to have a first charge. A polymer having a second charge opposite to the first charge can be disposed on the surface of the working electrode 110. The second charge on the polymer can attract the composition 120 and thereby, immobilize the composition 120 on the surface of the working electrode 110. Suitable charged polymers can include, but are not limited to quaternary ammonium salts, sulfonic acid salt polymers, and carboxylic acid salt polymers.

In some embodiments, a permeable membrane (not shown) can be disposed over the composition 120. The permeable membrane can ensure substantially stable diffusion of the target analyte to the composition 120 over the operational lifetime of the working electrode 110. Stable diffusion can ensure that any changes in the amperometric current measured by the electrochemical sensing system 100 is substantially due to a change in concentration of the target analyte and is not due to a variable flux of the target analyte to the composition 120. In some embodiments, the permeable membrane can be biocompatible. In some embodiments, the permeable membrane can also prevent fouling of the working electrode 110, for example, biofouling due to proteins present in a biological sample. In some embodiments, the permeable membrane can block interferents and reactive oxygen species; for example hydrogen peroxide and superoxide. Examples of materials which can be used to form the permeable membrane can include, for example, polyurethanes, silicones, epoxies, glutaraldehyde, acrylamides, acrylates, a sol-gel, any other suitable diffusivity layer or combination thereof.

The reference electrode 130 is electronically coupled to the working electrode 110 via the electrical circuit 140. The reference electrode 130 can include any suitable reference electrode that can provide a stable reference voltage for the working electrode 110 and does not get consumed by the oxidation or reduction reaction, thereby providing longer shelf life, no usage limitations due to reference consumption, and substantially reduce signal drift.

Suitable materials for the reference electrode 130 can include, for example, metal oxides (e.g., iridium oxide, ruthenium oxide, palladium oxide, platinum oxide, rhodium oxide), metal halides, conducting polymers (e.g., polyethylene dioxythiophene:polystyrene sulfonate (PEDOT:PSS), any other suitable stable reference electrode or combination thereof. In some embodiments, the reference electrode 130 can include rhodium and its oxides (e.g., $RhO_2$, $Rh(OH)_3$, $Rh_2O_3$, etc.). In some embodiments, the reference electrode 130 can include iridium and its oxides. In some embodiments, the reference electrode 130 can include palladium and its oxides.

The reference electrode 130 can have any shape or size. For example, in some embodiments, the reference electrode 130 can be a rod having a circular, oval, or polygonal cross-section. In some embodiments, the reference electrode 130 can be a needle type electrode which can, for example, be configured to be inserted into an animal or human body along with the working electrode 110. In some embodiments, the reference electrode 130 can be a flat electrode, for example, a flat plate, a disc, a solid state microfabricated electrode (e.g., of the type used in MEMS devices), or a screen printed electrode. In some embodiments, at least a portion of the reference electrode 130 can be insulated with an insulating material, for example, rubber, TEFLON®, plastic, parylene, silicon oxide, silicon nitride, any other suitable insulation material or combination thereof. The insulation material can, for example, be used to define an active area of the reference electrode 130. In some embodiments, the reference electrode 130 can have the same shape as the working electrode 110.

In some embodiments, a permeable membrane (not shown) can be disposed over the surface of the reference electrode 130, for example, to prevent fouling of the reference electrode. For example, proteins in a biological solution (e.g., blood) in which the target analyte is being detected, can adhere to the surface of the reference electrode, thereby fouling the reference electrode 130, which can cause the formal voltage of the reference electrode 130 to drift. The permeable membrane, for example, a biocompatible permeable membrane can prevent the proteins from adhering to the reference electrode, thereby reducing fouling. Examples of materials which can be used to form the permeable membrane can include, for example, polyurethanes, silicones, epoxies, glutaraldehyde, acrylamides, acrylates, a sol-gel, any other suitable diffusivity layer or combination thereof.

As shown in FIG. 1, the electrochemical sensing system 100 includes the working electrode 110 and the reference electrode 130 such that the electrochemical sensing system 100 is configured to operate in a two pole sensor system. The reference electrode 130 functions thereby as a pseudo-reference electrode, that is provides a reference voltage for the working electrode 110 to be biased against, as well as communicates electrons to or from the sample S (e.g., a liquid or gaseous sample) that includes the target analyte.

In some embodiments, the electrochemical sensing system 100 can further include a third counter electrode (not shown). In such embodiments, the electrochemical sensing system 100 can be operated in a three electrode configuration such that the electrons are communicated to or from the sample S via the counter electrode. In such embodiments, the reference electrode 130 only serves to provide an electronic reference for the working electrode 110.

The electrical circuit 140 is electronically coupled to the working electrode 110 and the reference electrode 130. In some embodiments, the electrical circuit 140 can include a transimpedance amplifier circuit configured to convert current to an amplified voltage. In some embodiments, the electrical circuit 140 can include an analog to digital converter configured to digitize the input current measurement. For example, the electrical circuit 140 can include a differential analog to digital converter which can increase noise rejection in the voltage measurement. The bias voltage can be communicated into a low end differential input of the analog to digital converter configured to provide a pseudo-negative range. This can, for example, allow digital filtering to remain accurate when noise remains in the low measurement range (e.g., to enhance the limit of detection). In some embodiments, the electrical circuit 140 can include operational amplifiers configured to amplify the measured signal. In some embodiments, the electrical circuit 140 can include a filtering circuit, for example, a low pass filter, a high pass filter, a band pass filter, any other suitable filtering circuit, or combination thereof, configured to substantially reduce signal noise. In some embodiments, the electrical circuit 140 can include a potentiostat circuit, for example, a programmable potentiostat circuit, configured to bias the working electrode 110 at the predetermined voltage. For example, the electrical circuit 140 can be configured to bias the working electrode 110 at a biasing voltage in the range of about −0.7 volts to about 0.4 volts, for example, about −0.6 V, about −0.5 V, about −0.3 V, about −0.1 V, about 0 V, about 0.1 V, about 0.2 V, or about 0.3 V, inclusive of all ranges therebetween. Furthermore, the electrical circuit 140 can be configured to measure a current corresponding to a concentration of the target analyte.

In some embodiments, the electrical circuit 140 can include a processor, e.g., a microcontroller, a microprocessor, an ASIC chip, an ARM chip, or a programmable logic controller (PLC). The processor can include signal processing algorithms, for example, band pass filters, low pass filters, any other signal processing algorithms or combination thereof. In some embodiments, the processor can be configured to control the bias voltage in real time, for example, to control one or more parameters of the redox reaction in real time. Such parameters can include, for example, electrochemical reaction rate and dynamic range which can be used to reverse or minimize the effects of electrochemical fouling and/or facilitate real time calibration. In some embodiments, the electrical circuit 140 can include a memory configured to store at least one of a redox current data, bias voltage data, user log, or any other information related to the electrochemical reaction. In some embodiments, the memory can also be configured to store a reference signature, for example, a calibration equation. In such embodiments, the processor can be configured to correlate the measured signal (e.g., the redox current) with the reference signature to determine the concentration of the target analyte.

In some embodiments, the electrochemical sensing system 100 can include a communications module (not shown). The communications module can be configured to allow two-way communication with a remote device e.g., a smart phone app, a local computer and/or a remote server. In some embodiments, the communications module can include a communication interface to provide wired communication with the external device, for example, a USB or FireWire interface. In some embodiments, the communications module can include means for wireless communication with the external device, for example, Wi-Fi, Bluetooth®, ANT+, low powered Bluetooth®, Zigbee and the like. In some embodiments, the communications module can include a RFID chip configured to store information, for example, the reference signature or sensing history, and allow a near field communication (NFC) device to read the stored information and/or update the stored information. In some embodiments, the electrochemical sensing system 100 can include a power source, for example, a rechargeable battery, configured to power the electrical circuit 140, the communications module or any other electronic component included in the electrochemical sensing system 100.

In some embodiments, the communications module can include a display configured to communicate information to the user, e.g., history of use, remaining battery life, wireless connectivity status, and/or visual reminders. In some embodiments, the communications module can also include microphones and/or vibration mechanisms to convey audio and tactile alerts. In some embodiments, the communications module can include a means for user input, for example, a button, a switch, and/or a touch screen, to provide an interface for input of at least one of power ON/OFF the electrochemical sensing system 100, reset the electrochemical sensing system 100, trigger communication between the electrochemical sensing system 100 and an external device, for example, a smart phone.

In some embodiments, the electrochemical sensing system 100 can be disposed in a housing (not shown) configured to house the components of the electrochemical sensing system 100. In some embodiments, the electrochemical sensing system 100 can be fixedly disposed in the housing. In some embodiments, one or more components of the electrochemical sensing system 100, for example, the working electrode 110 and/or the reference electrode 130 can be removably disposed in the housing. In such embodiments, the working electrode 110 and the reference electrode 130 can be configured to be replaced. In some embodiments, the housing can be substantially small such that the electrochemical sensing system 100 can be mounted on a user, for example, the skin of a user via an adhesive. For example, the housing can be configured to allow the working electrode 110 and the reference electrode 130 to pierce through the skin of a user and contact a bodily fluid, for example, blood, or interstitial fluid. The electrochemical sensing system 100 can thereby, be used to measure the concentration of a target analyte in the bodily fluid of the user in real time, for example, to provide real time health monitoring (e.g., glucose monitoring).

The sample S can be any sample which contains the target analyte. For example, the sample S can be a liquid sample, for example, a beverage, an environmental sample, a food sample, an agricultural sample, or a bodily fluid such as, for example, blood, urine, fecal matter solution, saliva, interstitial fluid, synovial fluid, cerebral fluid, sweat, tear drops, or any other bodily fluid. The sample S can be an in vitro sample, for example, disposed in a test container. In some embodiments, the sample S can be an in vivo sample, for example, a bodily fluid inside the body of a user (e.g., blood, interstitial fluid).

As described herein, in some embodiments, the composition 120 can be a synthetic redox-active receptor that is formulated to reversibly associate with the target analyte, such that the target analyte does not decompose. The composition 120 can have a first redox potential in the absence of a target analyte and a second redox potential different from the first redox potential in the presence of the target analyte. This variation in the redox potential of the composition 120 can be used to sense the target analyte. Equation 1 shows a possible sensing pathway of the composition 120:

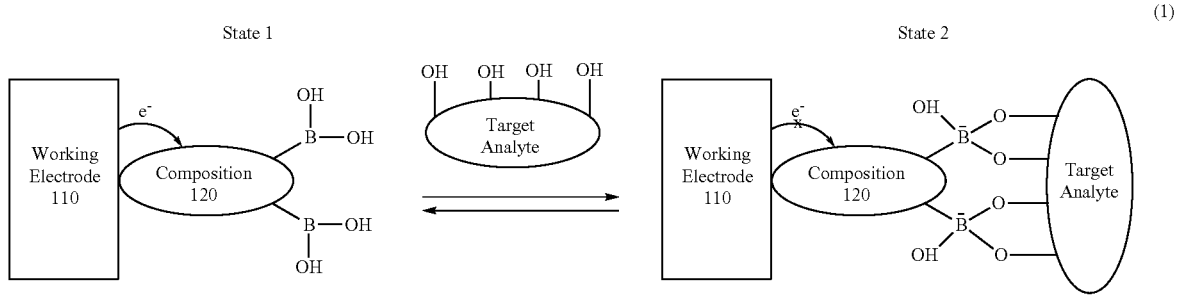

(1)

As shown in equation 1, the composition 120 can be disposed on the working electrode 110 using any suitable coupling mechanism described herein. The working electrode 110 can be biased voltage in the range of about −0.7 V to about 0.4 volts, for example, about −0.6 volts. In the absence of the target analyte, the composition 120 can be in state 1 where the composition 120 has the first redox potential and is capable of accepting an electron from the working electrode (i.e., can be reduced on the working electrode). A target analyte, for example, glucose, glutamate, lactic acid, dopamine, or any other target analyte described herein can then reversibly associate with the composition 120 and move the composition 120 to state 2. In some embodiments, composition 120 can be formulated to reversibly associate with the target analyte via esterification. In state 2, the composition 120 can have a second redox potential different from the first redox potential. For example, in state 2, the composition 120 can have a substantially higher redox potential than the first redox potential such that the composition 120 is less willing to accept an electron from the working electrode 120 (i.e., more difficult to be reduced). This shift in redox potential can be measured as a change in the redox current by the electrical circuit 140 which corresponds to the concentration of the target analyte. In this manner, the electrochemical sensing system 100 can sense the concentration of the target analyte in the sample S solution without consuming the target analyte.

Figure 2:
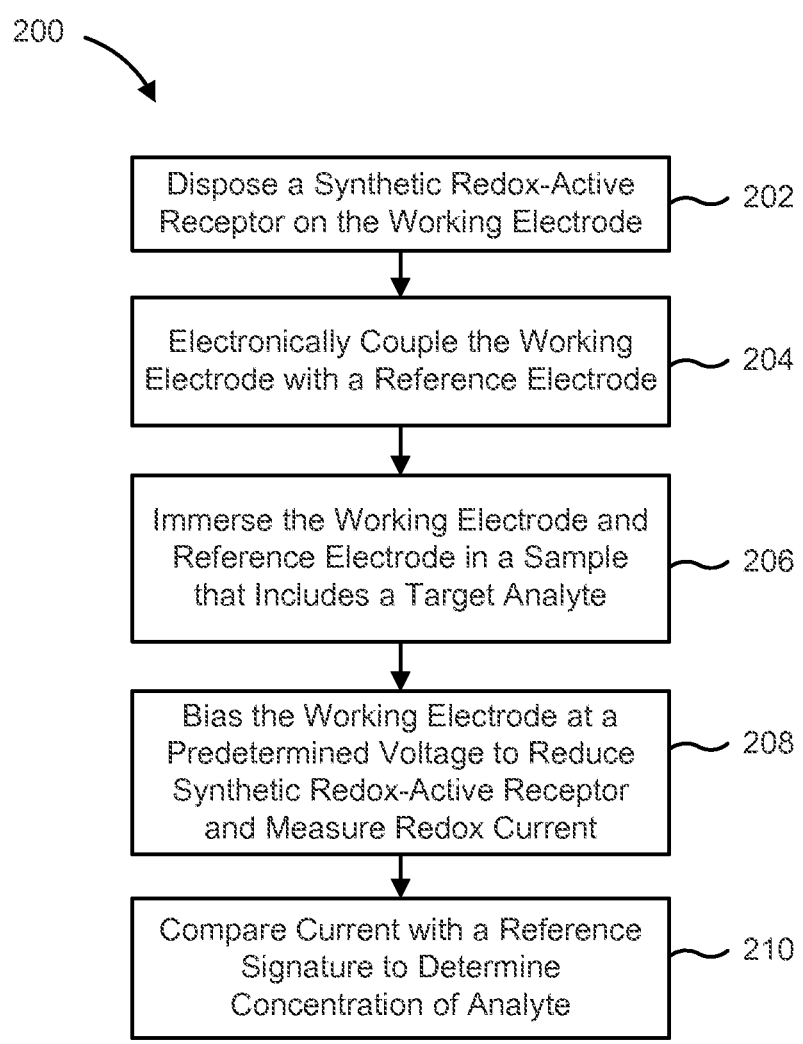
FIG. 2 is a schematic flow diagram showing a method of forming an electrochemical sensing system that includes a synthetic redox-active receptor, and sensing a target analyte present in a sample using the electrochemical sensing system, according to an embodiment.

FIG. 2 shows a flow diagram of an exemplary method of forming an electrochemical sensing system that includes a synthetic redox-active receptor and using the system for electrochemical sensing. First, a synthetic redox-active receptor is fixedly disposed on a working electrode 202. The working electrode can be any suitable working electrode, for example, rhodium, oxides of rhodium, chromium, titanium, nitinol, gold, platinum, oxides of platinum, nickel, palladium, oxides of palladium, iridium, oxides of iridium, stainless steel, carbon, graphite, carbon nanotubes, graphene, any other suitable working electrode. The synthetic redox-active receptor can be immobilized on the working electrode using any coupling methodology described herein. The synthetic redox-active receptor can include the salt of any one of formulas I-VIII, the composition having structure P-1, P-2, or any other composition described herein. Furthermore, the synthetic redox-active receptor can have a first redox potential in the absence of the target analyte.

The working electrode is then electronically coupled with a reference electrode 204, for example, the reference electrode 130 or any other reference electrode described herein. The electronic coupling can be performed via an electrical circuit configured to bias the working electrode at a predetermined biasing voltage and measure a redox current. The electrical circuit can include, for example, the electrical circuit 140 or any other electrical circuit described herein. The working electrode and the reference electrode are immersed or contacted with a sample that includes a target analyte whose concentration is being measured 206. The target analyte can include, for example, glucose, glutamate, lactic acid, dopamine, or any other target analyte described herein. The working electrode is biased at predetermined voltage, for example, about −0.6 volts to reduce the synthetic redox-active receptor and measure a redox current 208. The synthetic redox-active receptor can have a second redox potential different than the first redox potential in the presence of the target analyte such that the measured redox current changes corresponding to the concentration of the target analyte.

The measured current is compared with a reference signature, for example, a calibration plot, or a calibration equation to determine the concentration of the target analyte in the sample 210.

EXAMPLES

The following examples show electrochemical sensing of glucose performed using an electrochemical sensing system that includes a synthetic redox-active receptor. These examples are only for illustrative purposes and are not intended to limit the scope of the present disclosure.

Example 1: Sensing of Glucose with a Synthetic Redox-Active Receptor P-17

An electrochemical sensor for sensing glucose was prepared by disposing a synthetic redox-active receptor that included a boronic acid viologen having the structure P-17 as described herein, on a working electrode.

Figure 3:
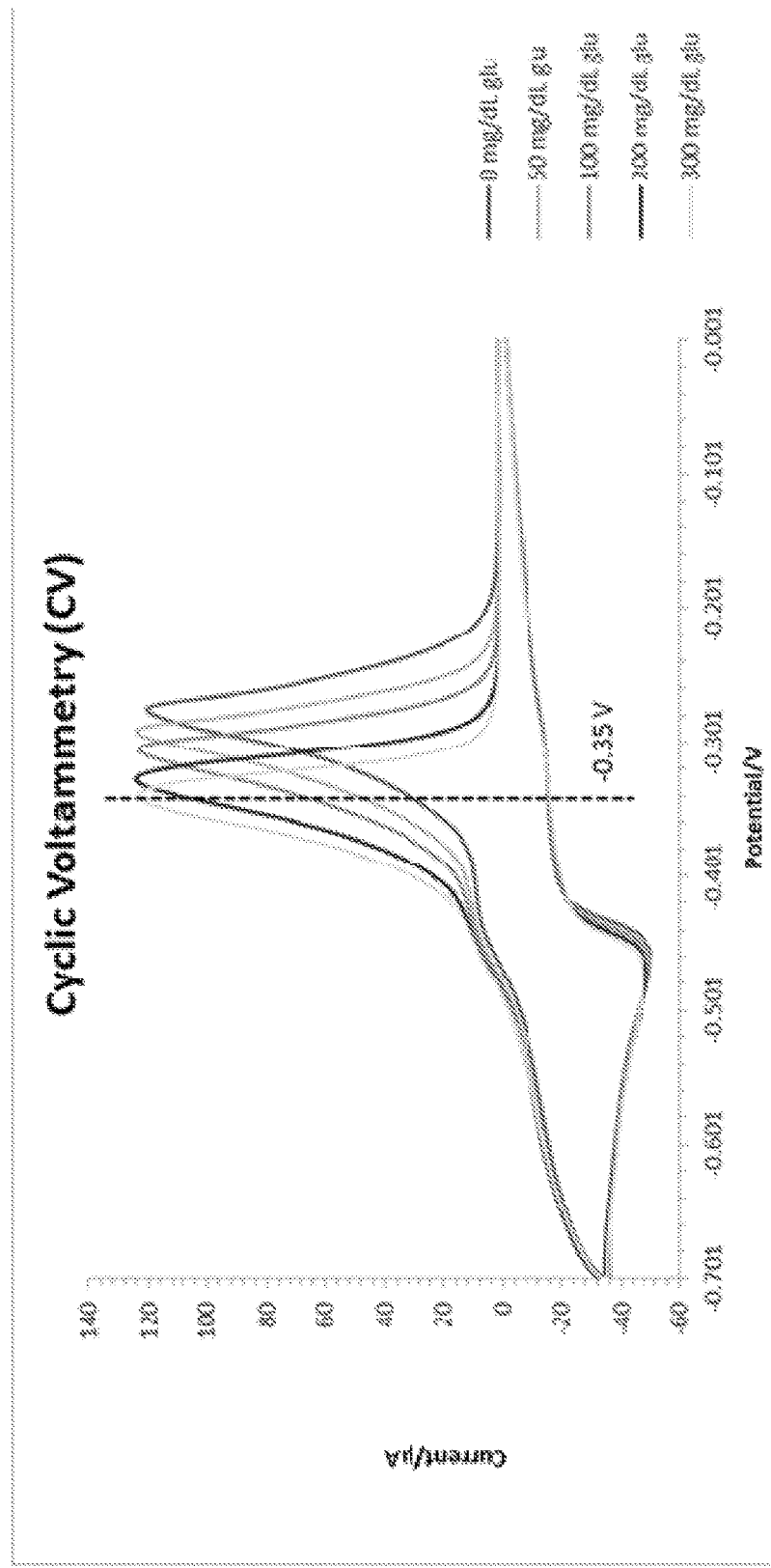
FIG. 3 is a plot showing the shift in redox potential of an electrochemical sensor that includes a synthetic redox-active receptor in response to increasing concentrations of glucose in a sample, analyzed using cyclic voltammetry.
Figure 4:
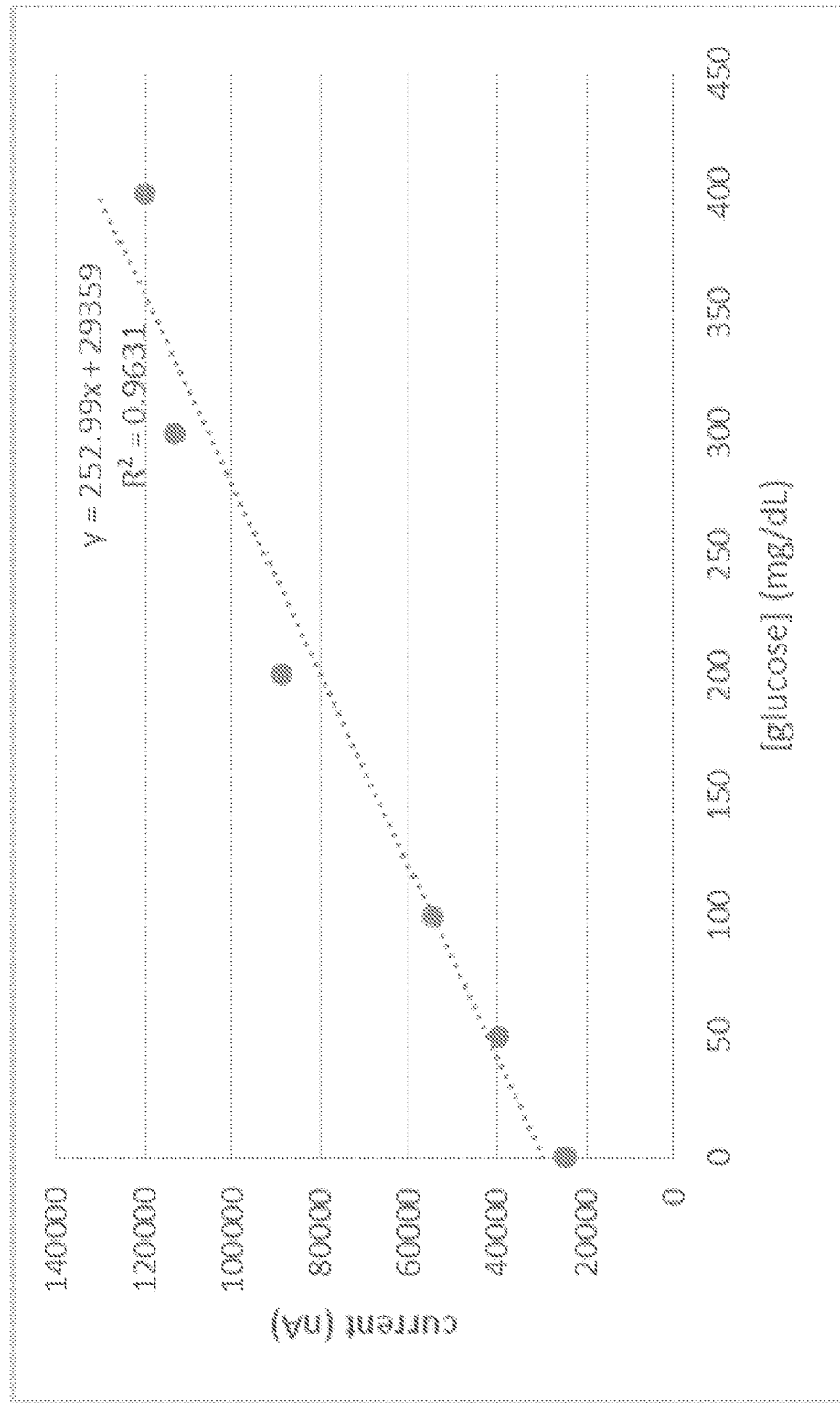
FIG. 4 is a plot of glucose concentration vs redox current of the electrochemical sensor of FIG. 3 measured at a biasing voltage of −0.35 volts.

The working electrode included a rhodium electrode that was formed by electroplating rhodium on a stainless steel wire. The working electrode was electronically coupled with a Ag/AgCl reference electrode and a platinum counter electrode via a PalmSens MultiTrace potentiostat. The working electrode was immersed in a sample solution that included 1 mg/mL of P-17 and 0.1M PBS. Cyclic voltammetry was performed to observe the redox behavior of the synthetic redox-active receptor in the sample solution. The voltage was swept between −0.7 volts and 0 volts. Increasing concentrations of glucose ranging between about 50 mg/dL, 100 mg/dL, 200 mg/dL, 300 mg/dL, and 400 mg/dL were added to the sample solution. Cyclic voltammetry was performed after each increase in concentration to observe the change in redox potential of the synthetic redox-active receptor. FIG. 3 shows cyclic voltammograms of the synthetic redox-active receptor in response to different concentrations of glucose. The redox peaks shifted towards the left. The shift in the redox peaks resulted in a current increase at −0.35 volts corresponding to the increasing concentration of glucose. FIG. 4 shows a plot of the glucose concentrations vs the redox current measured at −0.35 volts, extracted from the cyclic voltammograms shown in FIG. 3. The synthetic redox-active receptor demonstrated a linear increase in redox current corresponding to the increasing concentrations of glucose and had a sensitivity of about 252.99 nA/[mg/dL] of glucose.

Figure 5:
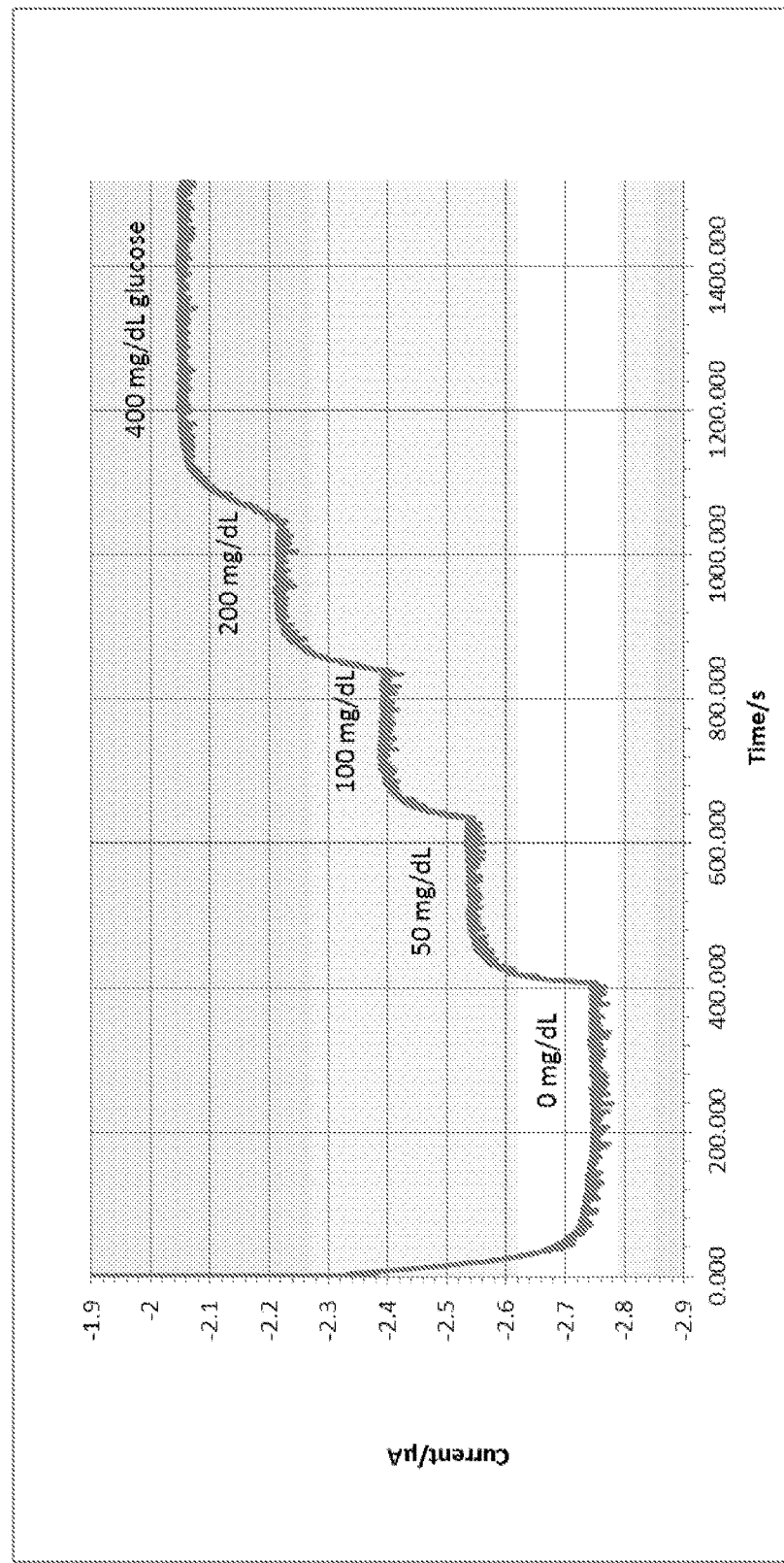
FIG. 5 is a plot of redox current as a function of time as increasing concentrations of glucose are added to the sample from 0 to 400 mg/dL using compound P-17 as a sensor.
Figure 6:
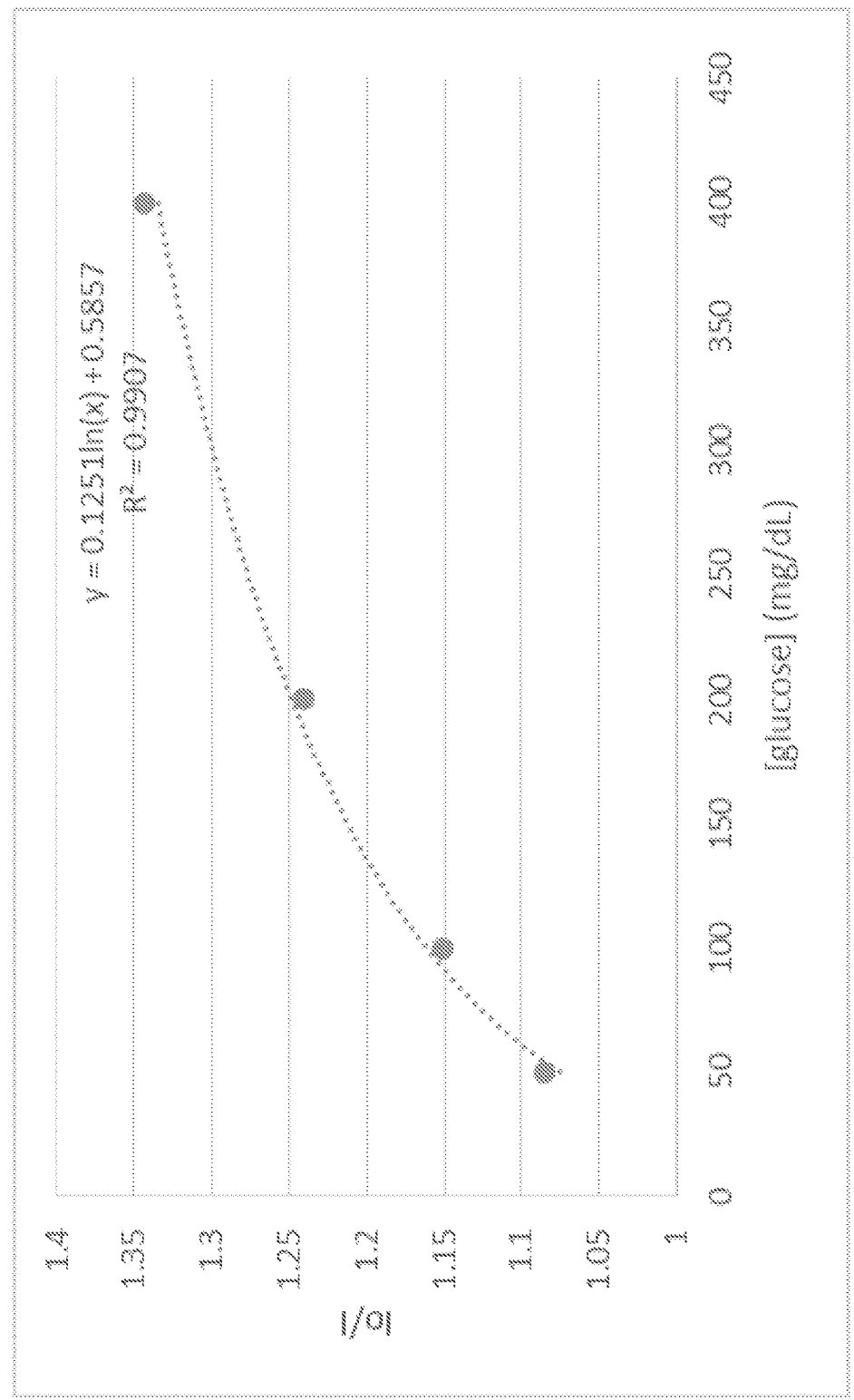
FIG. 6 is a plot of the ratio of control current to experimental current as a function of glucose concentration using compound P-17 as a sensor.

Compound P-17 was also entrapped in a membrane and used to measure glucose amperometrically. Compound P-17 (10 mg) was dissolved in water (1 g) with polyvinylpyrrolidone (0.2 g). The mixture was dipped onto a Platinum wire and dried at 60° C. for 30 min. The coated wire was dipped in an aqueous solution of polyurethane dispersion (0.8 g), vinyl imidazole (0.05 g), N-vinylpyrrolidone (0.05 g), and VA-044 (1 mg). The coated wire was heated at 60° C. under $N_2$ for 15 h. The coated wire was tested using a PalmSens MultiTrace potentiostat in multiple pulse amperometric mode. The sensor was placed in 100 mM PBS with Ag/AgCl as the counter/reference electrode and pulsed at −0.5 V for 0.1 s, 0 V for 0.1 s, and 0.5 V for 0.1 s. Aliquots of glucose were added and the change in current was recorded as a function of time. The relative change in current was plotted against glucose concentration as shown in FIG. 5. The relative ratio of control current to experimental current is given in FIG. 6.

Example 2: Sensing of Glucose with a Synthetic Redox-Active Receptor P-7

Compound P-7 was synthesized according to scheme 4.

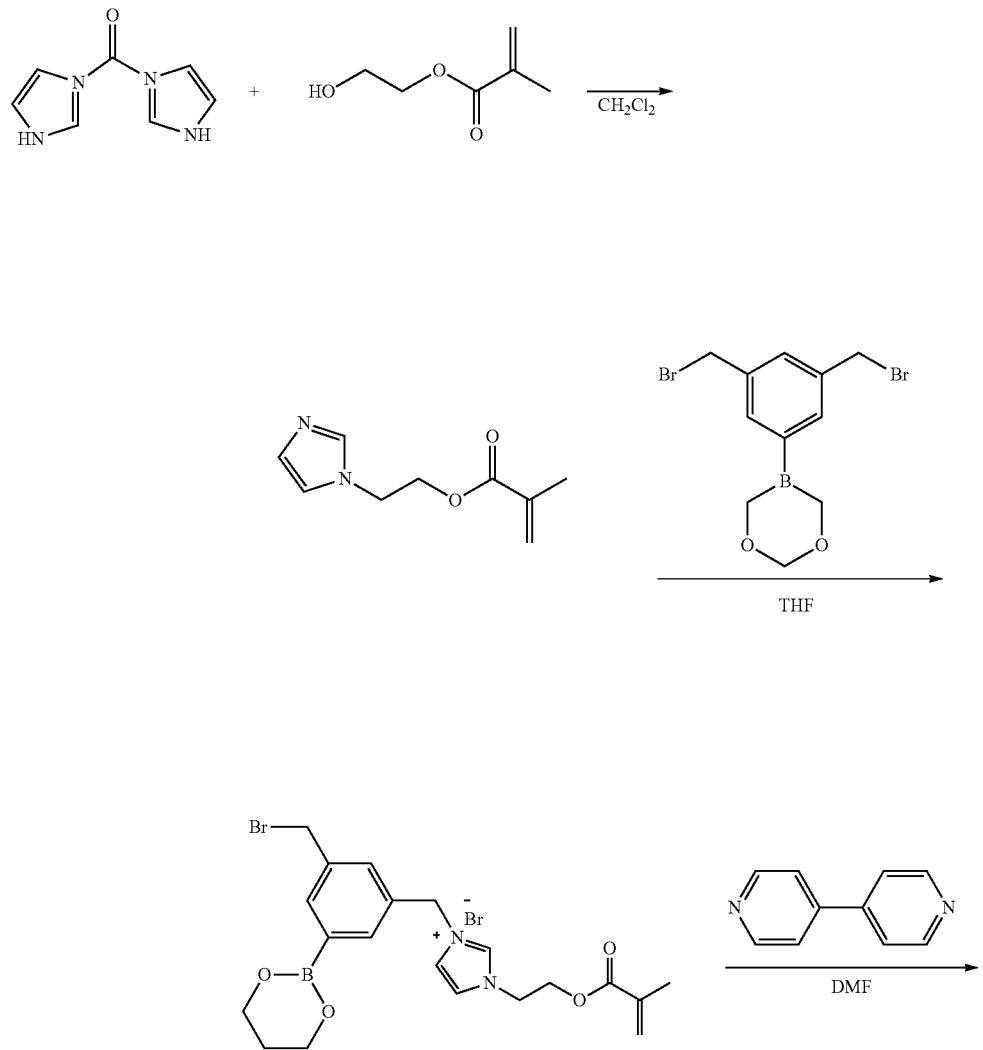

Scheme 4.

-continued

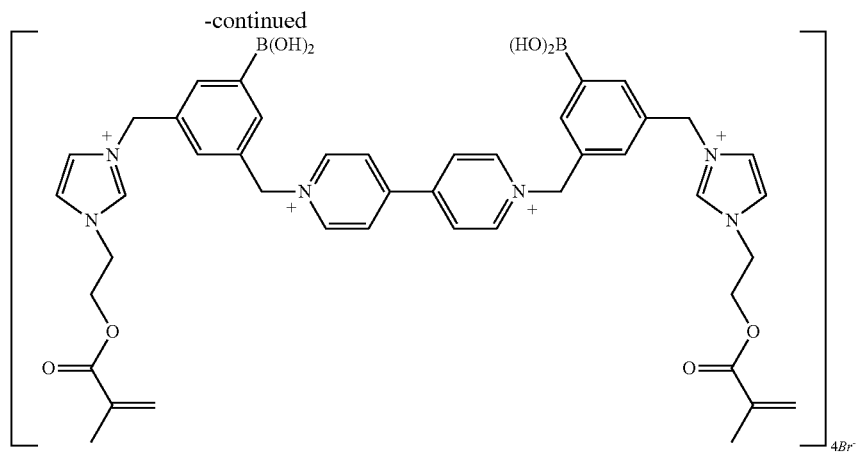

1,1'-Carbonyldiimidazole (3 mmols, 486 mg) was dissolved in CH2Cl2 (10 mL) with 2-hydroxyethylmethacrylate (1 mmol, 130 mg) and the solution was stirred at ambient temperature for 20 minutes. Water (10 mL) was added and the mixture was extracted with $CH_2Cl_2$ and dried over $MgSO_4$ to give a clear colorless oil (86 mg, 0.48 mmols, 48%). The product was dissolved in THF (5 mL) with 2-(3,5-bis-bromomethyl-phenyl)-[1,3,2]dioxaborinane (1.44 mmols, 0.5 g) and stirred at 40° C. for 72 h. The solution was concentrated in vacuo and the residue was triturated with acetone to give a white solid (0.178 g, 0.34 mmols, 70%). The product was dissolved in DMF (1 mL) with 4,4'-dipyridyl (0.15 mmols, 24 mg) and propylene glycol (0.1 mL) and heated at 55° C. for 72 h. Acetone (10 mL) was added to give a pale yellow precipitate that was washed with acetone and dried under vacuum to give a pale yellow solid (82 mg, 0.072 mmols, 48%) identified as P-7.

Figure 7:
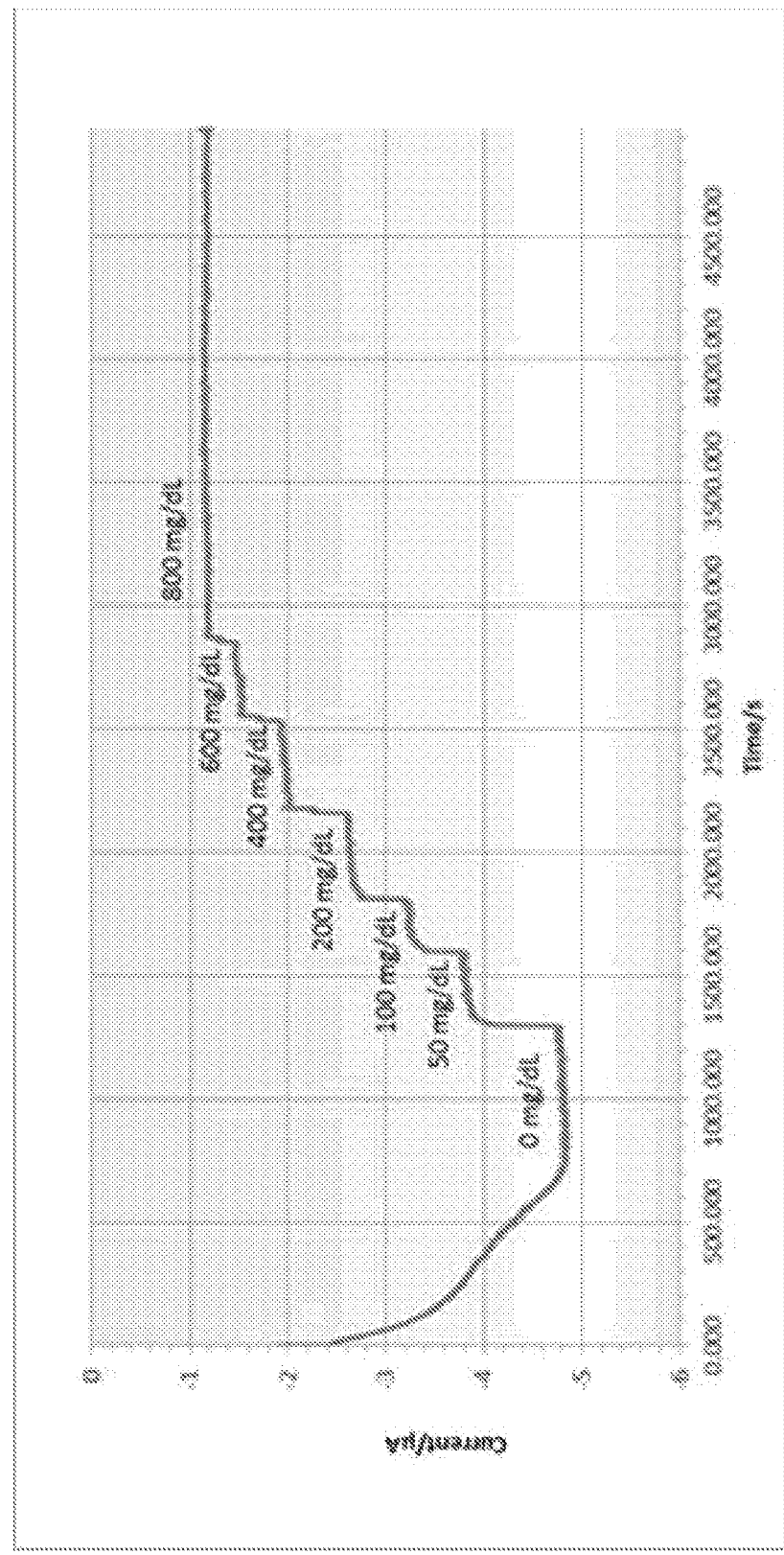
FIG. 7 is a plot of redox current as a function of time as increasing concentrations of glucose are added to a sample from 0 to 800 mg/dL using compound P-7 as a sensor.
Figure 8:
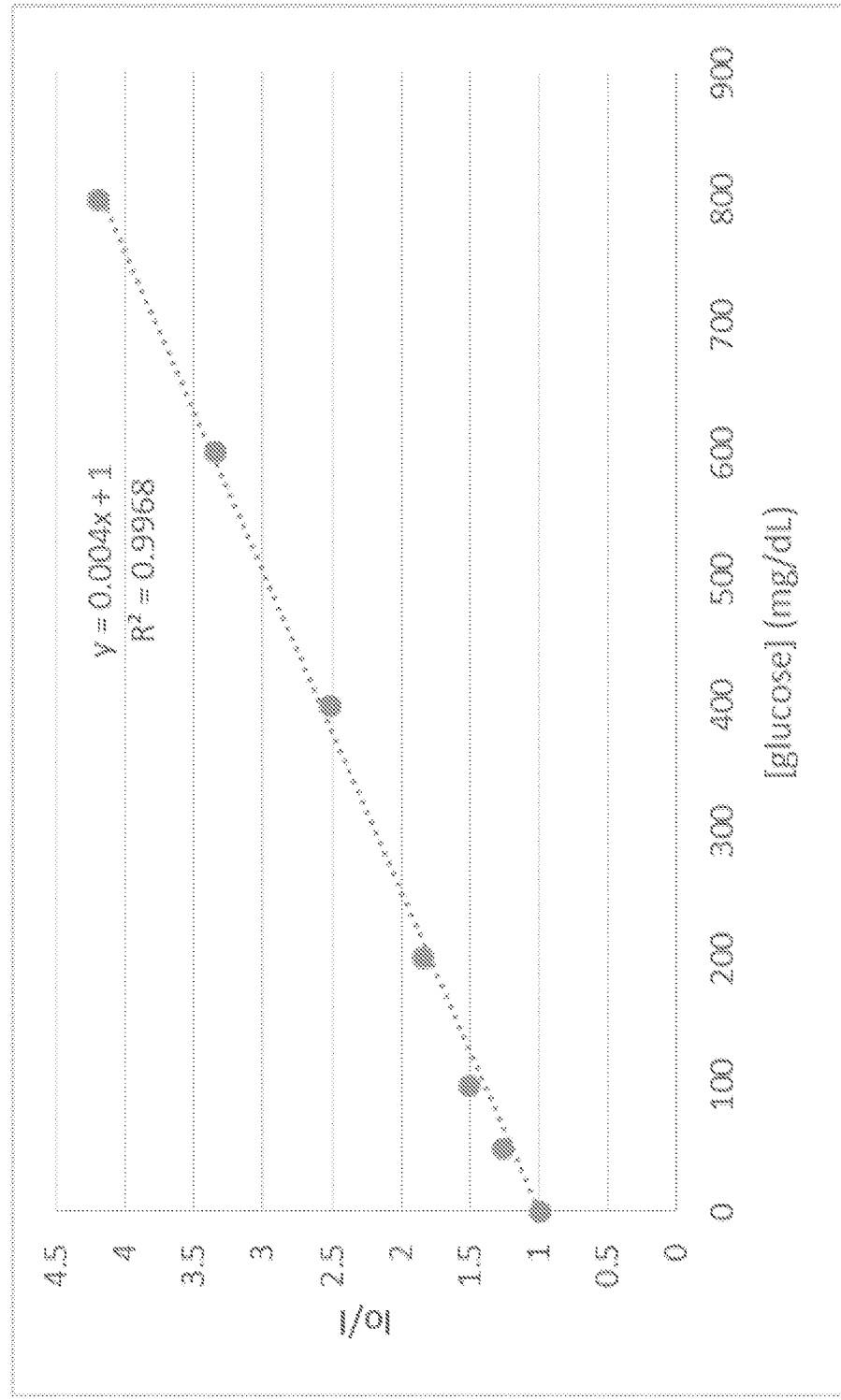
FIG. 8 is a plot of the ratio of control current to experimental current as a function of glucose concentration using compound P-7 as a sensor.

Compound P-7 was immobilized into a membrane and used to measure glucose amperometrically. Compound P-7 (10 mg) was dissolved in water (0.4 g) with polyvinylpyrrolidone (0.03 g), 2-hydroxyethylmethacrylate (20 µL), N,N-dimethylacrylamide (20 µL), N,N-methylenebis(acrylamide) (0.4 mg) and VA-044 (1 mg). The mixture was dipped onto a Platinum wire and heated at 50° C. for 15 h under $N_2$. The coated wire was dipped in an aqueous solution of polyurethane dispersion and heated at 50° C. for 30 min. The coated wire was tested using a PalmSens MultiTrace potentiostat in multiple pulse amperometric mode. The sensor was placed in 100 mM PBS with Ag/AgCl as counter/reference electrode. The system was pulsed at −0.55 V for 0.1 s, 0 V for 0.1 s, and 0.55 V for 0.1 s. Aliquots of glucose were added and the change in current over the range of 0-800 mg/dL glucose was recorded as a function of time. The relative change in current was plotted against glucose concentration as shown in FIG. 7. The relative ratio of control current to experimental current is given in FIG. 8.

Figure 9:
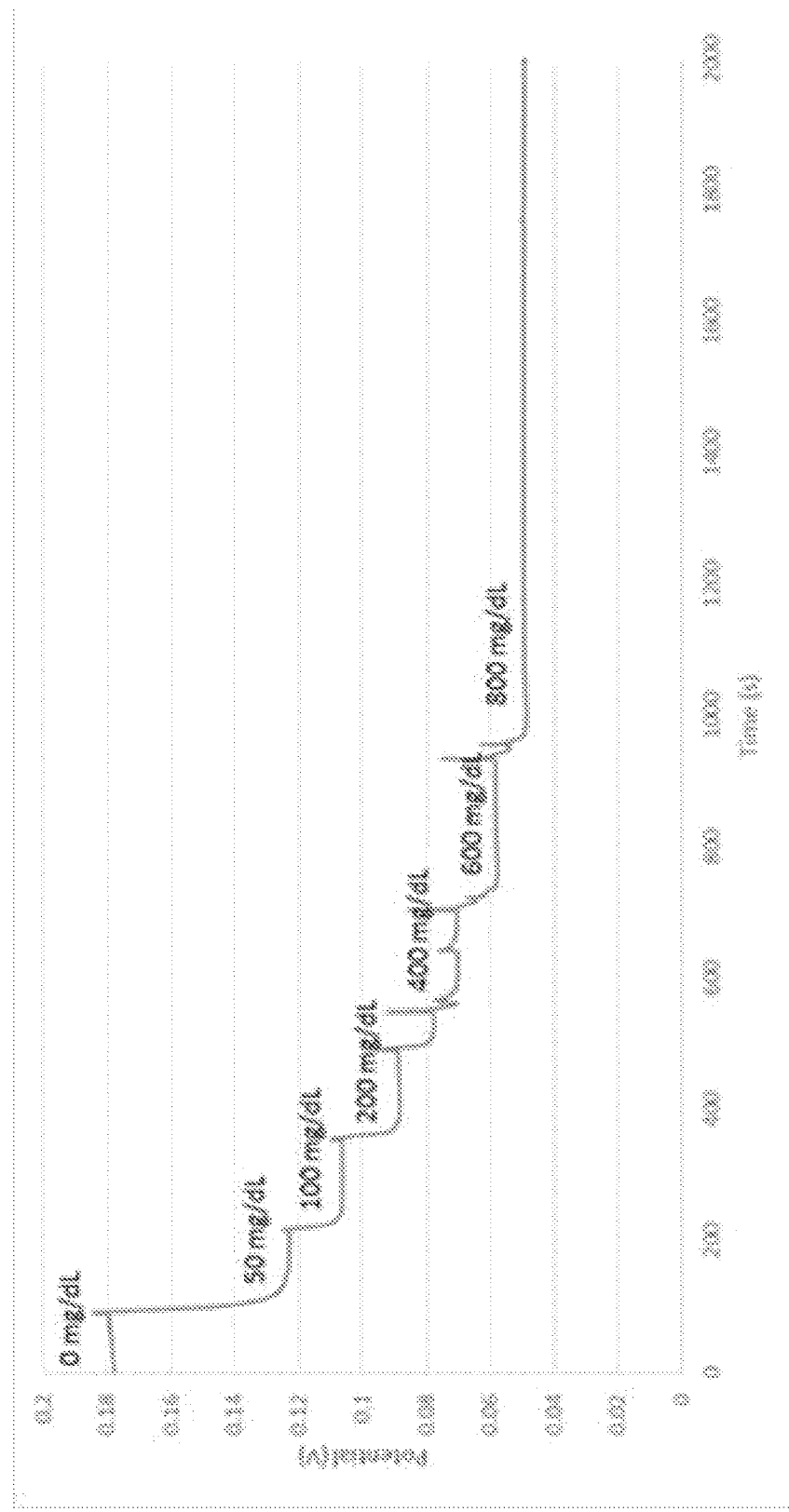
FIG. 9 shows a plot of voltage potential over time as increasing amounts of glucose are added.
Figure 10:
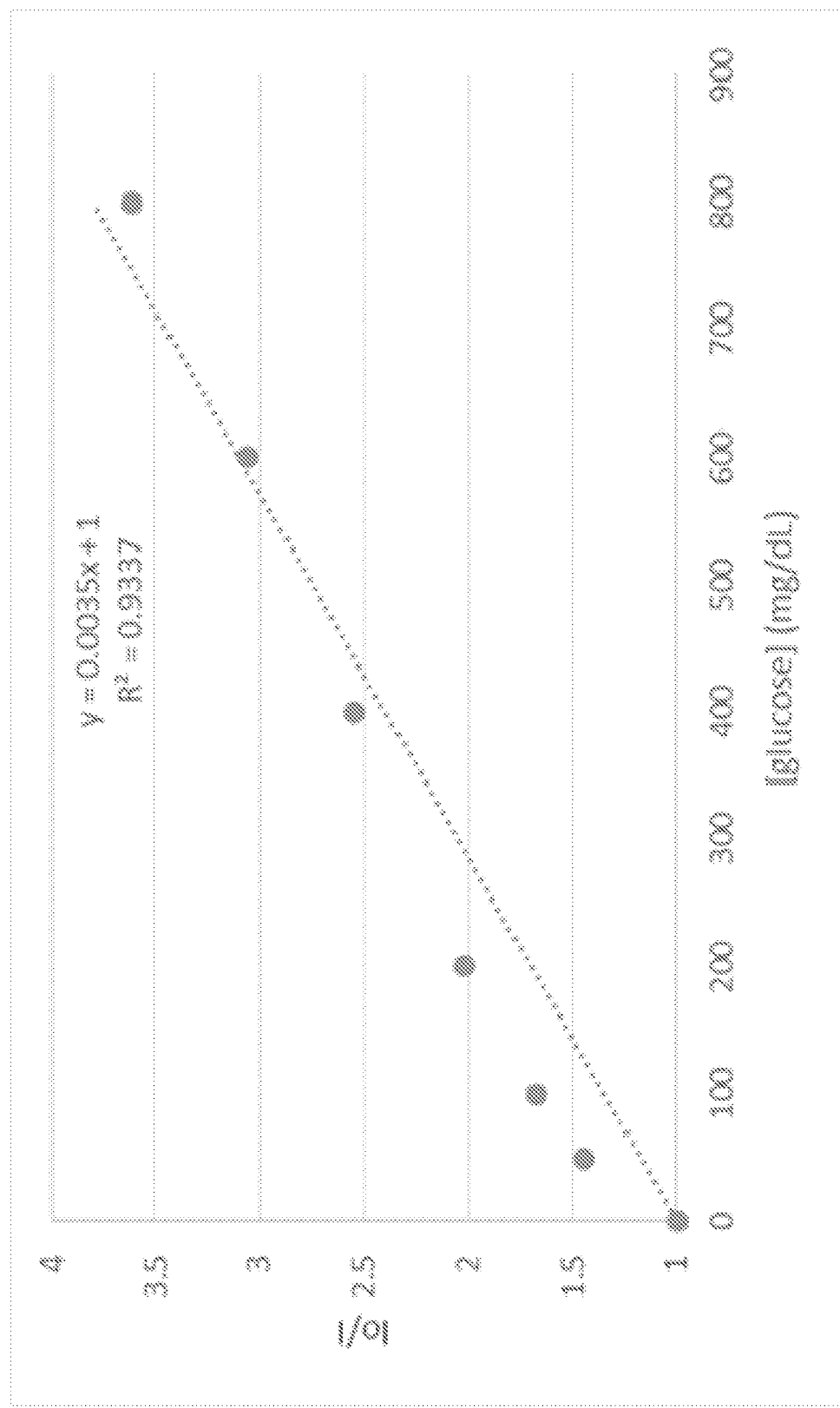
FIG. 10 shows a plot of control current over current at increasing glucose concentrations.

The same sensor was also tested in potentiometric (open circuit) 0 volts mode using a rhodium-plated hypodermic needle as the reference electrode. The relative change in voltage was plotted against glucose concentration. FIG. 9 shows a plot of voltage potential over time as increasing amounts of glucose are added. FIG. 10 shows a reference current Over Current at Increasing Glucose Concentrations.

Example 3: Sensing of Glucose with a Synthetic Redox-Active Receptor Dihydrobenzodiimidazole An electrochemical sensor for sensing glucose is prepared by disposing a synthetic redox-active receptor that includes a boronic acid viologen having a dihydrobenzodiimidazole diium structure as described herein (e.g., P-15, P-14), on a working electrode.

The working electrode includes a rhodium electrode that is formed by electroplating rhodium on a stainless steel wire. The working electrode is electronically coupled with an Ag/AgCl reference electrode and a platinum counter electrode via a PalmSens MultiTrace potentiostat. The working electrode is immersed in a sample solution that includes 1 mg/mL of P-15 and 0.1M PBS. Cyclic voltammetry is performed to observe the redox behavior of the synthetic redox-active receptor in the sample solution. The voltage is swept between −0.7 volts and 0 volts. Increasing concentrations of glucose ranging between about 50 mg/dL, 100 mg/dL, 200 mg/dL, 300 mg/dL, and 400 mg/dL are added to the sample solution. Cyclic voltammetry is performed after each increase in concentration to observe the change in redox potential of the synthetic redox-active receptor. The synthetic redox-active receptor is expected to demonstrate a linear increase in redox current corresponding to the increasing concentrations of glucose and to have a sensitivity of about 252.99 nA/[mg/dL] of glucose.

A dihydropyrroloindole such as compound P-15 is also entrapped in a membrane and used to measure glucose amperometrically.

Compound P-17 (10 mg) is dissolved in water (Ig) with polyvinylpyrrolidone (0.2 g). The mixture is dipped onto a Platinum wire and dried at 60° C. for 30 min. The coated wire is dipped in an aqueous solution of polyurethane dispersion (0.8 g), vinyl imidazole (0.05 g), N-vinylpyrrolidone (0.05 g), and VA-044 (1 mg). The coated wire is heated at 60° C. under $N_2$ for 15 h. The coated wire is tested using a PalmSens MultiTrace potentiostat in multiple pulse amperometric mode. The sensor is placed in 100 mM PBS with Ag/AgCl as the counter/reference electrode and pulsed at −0.5 V for 0.1 s, 0 V for 0.1 s, and 0.5 V for 0.1 s. Aliquots of glucose are added and the change in current is recorded as a function of time.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. An electrochemical sensing system, comprising:
a working electrode;
a composition disposed on the working electrode;
a reference electrode;
an electrical circuit electronically coupled to the working electrode and the reference electrode, the electrical circuit configured to measure a current or voltage corresponding to a concentration of a target analyte;
wherein the composition comprises a salt of formula (Va):

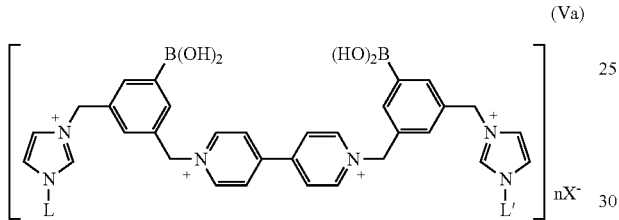

(Va)

where:
$X^-$ is an anion;
L and L' are independently H, halogen, OH, CN, $C_1$-$C_6$ alkyl, $C_2$-$C_6$ alkenyl, $C_2$-$C_6$ alkynyl, aryl, heteroaryl, heterocyclyl, cycloalkyl, alkylthio, arylthio, alkoxy, aryloxy, —$COOR^4$, $NH_2$, —C(O)N(H)—$(CH_2)_p$—N(H)C(O)—$R^4$, —C(O)NH($R^4$), or —N(H)C(O)$R^4$;
$R^4$ is independently at each occurrence H, $C_1$-$C_6$ alkyl, $C_2$-$C_6$ alkenyl, $C_2$-$C_6$ alkynyl, aryl, heteroaryl, heterocyclyl, or cycloalkyl;
n is 2, 3, 4, 5, or 6; and
p is independently 0, 1, 2, 3, 4, 5, or 6.

2. The electrochemical sensing system of claim 1, wherein the composition is immobilized in a polymer.

3. The electrochemical sensing system of claim 1, wherein at least a portion of the working electrode comprises at least one of a rhodium, oxide of rhodium, gold, platinum, and palladium.

4. The electrochemical sensing system of claim 1, wherein the target analyte is a diol, dopamine, glucose, glutamate, alpha hydroxy acid or lactic acid.

5. The electrochemical sensing system of claim 1, wherein the composition is formulated to reversibly associate with the target analyte by esterification.

6. The electrochemical sensing system of claim 1, wherein the reference electrode includes at least one of a rhodium and its oxides, iridium and its oxides, and palladium and its oxides.

7. The electrochemical sensing system of claim 1, wherein the reference electrode includes silver/silver chloride.

8. The electrochemical sensing system of claim 1, wherein the electrical circuit is configured to bias the working electrode at a biasing voltage, and wherein the biasing voltage is about −0.7 volts, about −0.6 volts, about −0.5 volts, about −0.4 volts, about −0.3 volts, about 0 volts or about 0.4 volts.

9. An electrochemical sensing method for determining a target analyte concentration, the electrochemical sensing method comprising: determining the target analyte concentration via amperometric measurement, pulsed amperometric measurement, differential pulse measurement or potentiometry, utilizing the electrochemical sensing system of claim 1.

10. An electrochemical sensing system, comprising:
a working electrode,
a composition disposed on the working electrode,
a reference electrode,
an electrical circuit electronically coupled to the working electrode and the reference electrode, the electrical circuit configured to measure a current or voltage corresponding to a concentration of a target analyte;
wherein the composition comprises a compound having the structure:

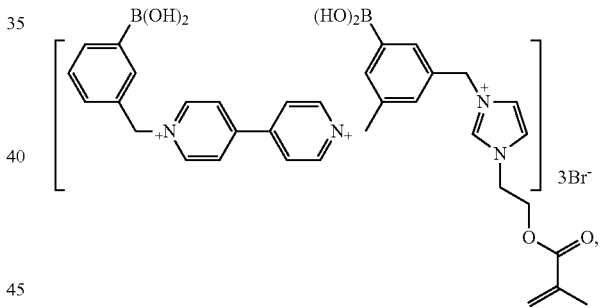

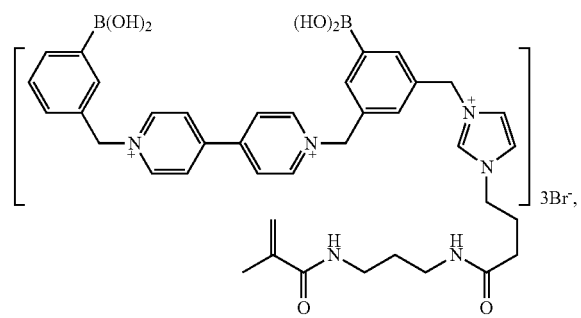

45 46
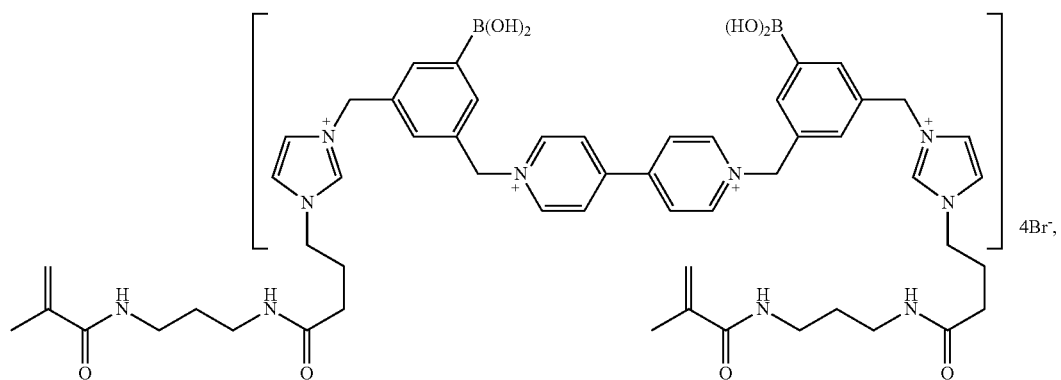
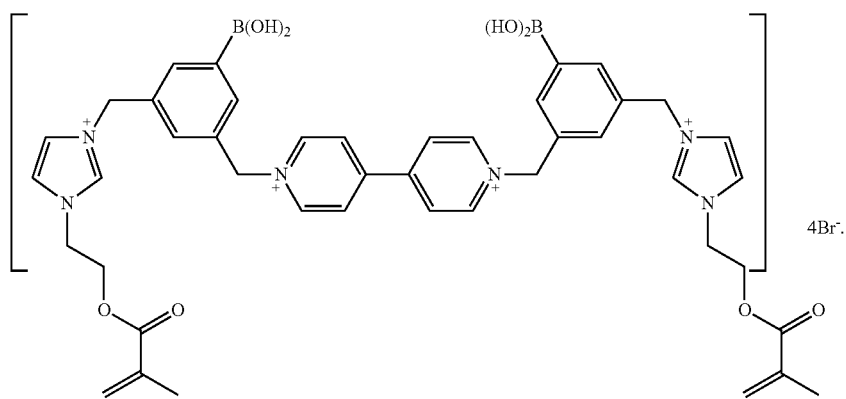
* * * * *